US011260118B2

(12) United States Patent
Chai et al.

(10) Patent No.: US 11,260,118 B2
(45) Date of Patent: Mar. 1, 2022

(54) IMMUNOGENIC PEPTIDE COMPOSITION

(71) Applicant: Cancer Research Malaysia, Selangor (MY)

(72) Inventors: San Jiun Chai, Selangor (MY); Sammuel Chee Yong Fong, Selangor (MY); Chai Phei Gan, Selangor (MY); Sathibalan Ponniah, Selangor (MY); Vyomesh Patel, Selangor (MY); Sok Ching Cheong, Selangor (MY); Kue Peng Lim, Selangor (MY)

(73) Assignee: Cancer Research Malaysia, Selangor (MY)

( * ) Notice: Subject to any disclaimer, the term of this patent is extended or adjusted under 35 U.S.C. 154(b) by 156 days.

(21) Appl. No.: 16/494,580

(22) PCT Filed: Mar. 15, 2018

(86) PCT No.: PCT/MY2018/050011
§ 371 (c)(1),
(2) Date: Sep. 16, 2019

(87) PCT Pub. No.: WO2018/169385
PCT Pub. Date: Sep. 20, 2018

(65) Prior Publication Data
US 2020/0138929 A1    May 7, 2020

(30) Foreign Application Priority Data

Mar. 15, 2017   (MY) .......................... PI 2017700886

(51) Int. Cl.
*A61K 39/00* (2006.01)
*A61P 35/00* (2006.01)
*A61K 39/395* (2006.01)
*A61K 45/06* (2006.01)

(52) U.S. Cl.
CPC .............. *A61K 39/001186* (2018.08); *A61K 39/001162* (2018.08); *A61K 39/3955* (2013.01); *A61K 45/06* (2013.01); *A61P 35/00* (2018.01)

(58) Field of Classification Search
None
See application file for complete search history.

(56) References Cited

U.S. PATENT DOCUMENTS

2016/0030536 A1 *   2/2016   Weiner .................... A61P 35/02
                                                                    424/85.2

FOREIGN PATENT DOCUMENTS

| WO | WO2010147452   | * 12/2012 | ............... C12Q 1/68 |
| WO | WO 2013009165 A1 | 1/2013 | |
| WO | WO 2013098797 A2 | 7/2013 | |

OTHER PUBLICATIONS

Chai, S. J. et al. "Identification of four-jointed box 1 (FJXI)—Specific peptides for immunotherapy of nasopharyngeal carcinoma", PLOS One, 2015, vol. 10, Issue 11, 21 pages.
Chai, S. J. et al. "Identification of Fjx1 as a biomarker for the development of a novel peptide vaccine for nasopharyngeal carcinoma (NPC)", Malaysian Journal of Pathology, The Immunology Symposium (Abstracts), Malaysia, 2014, Poster Presentation, P9, pp. 234-235.
Lim, K. P. et al. "Identification of Immunogenic MAGED4B peptides for vaccine development in oral cancer immunotherapy", Human Vaccines & Immunotherapeutics, 2014, vol. 10, Issue 11, pp. 3214-3223.
Lim, K. P. et al. "From target identification to peptide vaccine development for oral cancer", Malaysian Journal of Pathology, The Immunology Symposium (Abstracts), Malaysia, 2014, p. 235.

* cited by examiner

*Primary Examiner* — Elly-Gerald Stoica
(74) *Attorney, Agent, or Firm* — Muncy, Geissler, Olds & Lowe, P.C.

(57) ABSTRACT

The present invention relates to a peptide composition capable of binding with major histocompatibility complex class I molecules to induce an anti-cancer immune response in a subject. Particularly, the peptide composition comprises at least a Four-jointed Box 1 peptide and a Melanoma Antigen family D4b peptide. The present invention further relates to the use of a peptide composition and a peptide vaccine for inducing the anti-cancer immune response in the subject.

12 Claims, 12 Drawing Sheets
Specification includes a Sequence Listing.

(a)

(b)

(a)

(b)

(c)

IMMUNOGENIC PEPTIDE COMPOSITION

TECHNICAL FIELD OF THE INVENTION

The present invention relates to a peptide composition for enhancing anti-tumour response in a patient in need thereof.

BACKGROUND OF THE INVENTION

Head and neck squamous cell carcinoma (HNSCC) is the sixth most common cancer behind lung, breast, stomach, colorectal, and liver cancers (Ferlay et al., 2015). As squamous cells are found in the outer layer of skin and in the mucous membranes, HNSCC develops in the mucous membranes of the mouth, nose, and throat.

At present, treatment options remain limited to surgery, radiotherapy, and chemotherapy. A newer type of cancer therapy option, targeted therapy, includes the use of a drug that targets cancer cells. Currently, the only approved targeted therapy for HNSCC by the US Food and Drug Administration (FDA) is cetuximab, which target cancer cells by acting as an inhibitor for epidermal growth factor receptor (EGFR). When patients received a treatment combination of chemotherapy with cetuximab, the median overall survival duration improved by 2.6 months, compared against patients who only received chemotherapy (Vermorken et al., 2008).

Given that the survival duration of these patients only improved slightly, an alternative cancer treatment has since been warranted. Immunotherapy, a treatment which relies on a patient's immune system to fight cancer by stimulating an immune response, includes different treatments which work in different ways. Some immunotherapy treatments are used to remove the inhibition of the body's immune system, while other immunotherapy treatments work to train the immune system to detect and attack cancer cells specifically.

Immunotherapy has been shown to be a plausible approach for treating HNSCC, as emerging studies have demonstrated the presence of high mutational loads and high levels of tumour infiltrating lymphocytes in HNSCC patients. Nasman et al. 2012 further reports the positive correlation between the high density of infiltrating $CD8^+$ T cells with clinical outcome in patients with both Human Papillomavirus Infection positive ($HPV^+$) and negative ($HPV^-$) tonsillar squamous cell carcinoma, highlighting the immunogenic properties of HNSCC.

Two examples of FDA approved immunotherapy treatments are nivolumab and pembrolizumab, both of which are anti-programmed cell death protein 1 (PD-1) monoclonal antibodies used in the treatment of advanced melanoma, non-small cell lung cancer, and renal cell carcinoma. These immune checkpoint inhibitors have shown promising results in treating head and neck cancer patients, with the overall survival rate of HNSCC patients at 36% when a group of HNSCC patients received nivolumab, compared to a survival rate of 16% in a standard therapy group. Further, these patients in the former group survived 2.4 months longer compared to the patients in the latter group, with fewer grade 3 or grade 4 events reported (Ferris et al., 2016).

The objective response rate, that is, a complete response or a partial response of tumour size reduction, in patients who received pembrolizumab for treating recurrent or metastatic HNSCC was 16%.

These results are encouraging, yet despite the promising efficacy of available checkpoint inhibitor immunotherapy, a large proportion of treatment patients have yet to respond to the therapy. Whilst not completely understood, it is believed that the absence of strong pre-existing anti-tumour immune response in subjects could deter the efficiency of the drug, as anti-tumour immunity is critical in influencing the tumour stage and controlling metastasis.

As such, there is therefore a need for an alternative immunotherapy approach which is able to enhance the anti-tumour immune response in a subject, which consequently enhances the efficacy of current immunotherapies.

SUMMARY OF THE INVENTION

An objective of the present invention is to therefore provide a peptide composition capable of inducing an anti-cancer response in a patient.

Another objective of the present invention is to provide a peptide composition capable of delaying the growth of tumour in a patient.

A further objective of the present invention is to provide a peptide vaccine for inducing an anti-cancer immune response in a patient.

These and other objectives of the invention are achieved through the use of a peptide composition, characterised in that the peptide composition comprises at least a Four-jointed Box 1 (FJX1) peptide and a Melanoma antigen family D4b (MAGED4b) peptide.

More specifically, in accordance with the present invention, the peptide composition, PV1, comprises a FJX1 peptide (F1) and a MAGED4b peptide (M6), which binds with major histocompatibility complex (MHC) Class I molecules for inducing an anti-cancer immune response in a subject.

A second aspect of the invention relates to a peptide vaccine according to PV1, wherein said peptide vaccine comprises at least a M6 peptide and a F1 peptide for inducing an anti-cancer immune response in a subject by binding with MHC Class I molecules.

The invention further relates to the use of an amount of F1 and M6 peptides in the manufacture of a medicament for treating any one or a combination of head and neck squamous cell carcinoma (HNSCC), breast cancer, colon cancer, rectum cancer, lung cancer, prostate cancer or any other cancer types expressing FJX1 or/and MAGED4B in a subject in need thereof, wherein the medicament is capable of binding with MHC Class I molecules to induce an anti-cancer immune response in the subject.

As F1 and M6 peptides are MHC Class I-specific, it is therefore preferable that the peptide composition is provided only to subjects with matching HLA subtypes.

BRIEF DESCRIPTION OF THE DRAWINGS

FIG. 1(a) illustrates the representative images of intensity scores for IHC staining. FIG. 1(b) shows the percentage of patients with FJX1 and MAGED4b expressions.

As seen in FIG. 2, PV1 peptides can be recognized by higher population of T cells compared to single peptide, either F1 or M6, alone.

FIG. 3(a) shows interferon gamma (IFNγ) and FIG. 3(b) shows granzyme B secretion in the ex vivo and cytotoxic (CTX) ELISPOT assays.

FIG. 4(a) shows representative images of different intensities of FJX1 and MAGED4b stains of tumour tissues. FIG. 4(b) indicates the IFNγ and granzyme B secretion in response to PV1 stimulation in the cytotoxic ELISPOT assay and correlates with the levels of FJX1 and MAGED4B expression in patients' biopsies. FIG. 4(c) shows PBMCs/T cells from patients' whose tumour highly expresses at least 1 target antigen is more readily being stimulated and secretes higher levels of IFNγ and granzyme B secretion in response to PV1 stimulation compared to tumour with that have negligible expression of MAGED4B and FJX1

FIG. 6(a) indicates that mice vaccinated with PV1 shows a significant increase in the T cells that can react against PV1 loaded dimers, compared to only baseline or negligible response when exposed to non-loaded and irrelevant peptide loaded dimers. FIG. 6(b) shows that mice vaccinated with PV1 are able to recognise T2 cells presenting PV1 peptides in the ex vivo ELISPOT and induce IFNγ secretion in a dose dependent manner.

FIG. 10(a) indicates the expression of MAGED4b and FJX1 in 16 ORL lines (oral cancer cell line), FIG. 10(b) shows that expression of MAGED4b and FJX1 in immortalised NP/NPC cell lines (nasopharynx or nasopharyngeal carcinoma cell line). FIG. 10(c) demonstrated the expression of MAGED4B is undetected in normal oral keratinocytes while FJX1 is detected at low levels.

DETAILED DESCRIPTION OF THE INVENTION

Figure 1:
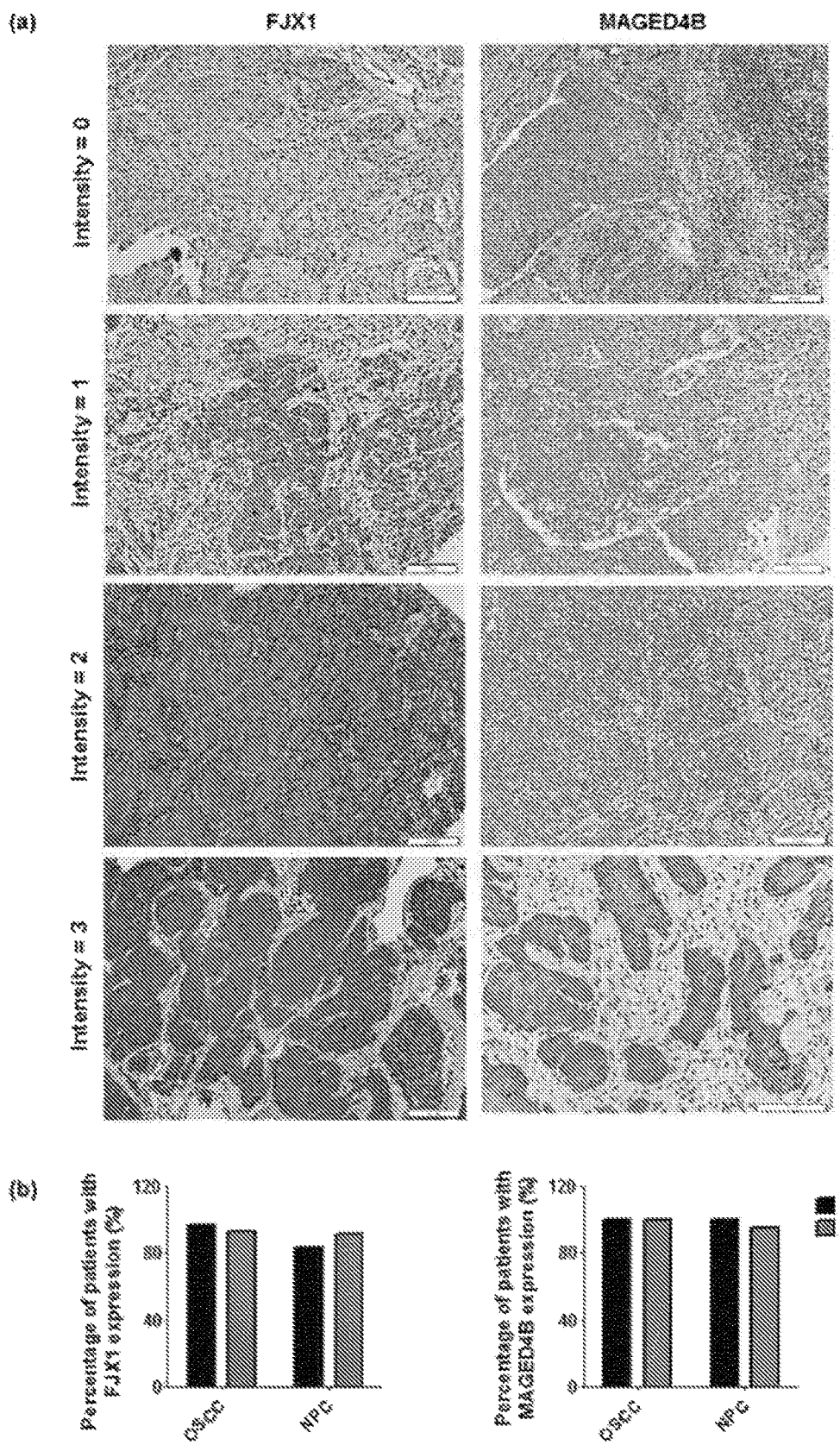
FIG. 1 relates to the expression of MAGED4b and FJX1 in HNSCC samples.

The embodiment of the present invention will now be described in a more detailed manner, where examples of the preferred embodiment and the scope of the invention will be fully conveyed to those skilled in the art. However, it should be understood that the present disclosure is not intended to limit the invention to the precise forms as disclosed, but rather, provided so that the disclosure will be thorough and complete.

Peptide vaccine, a form of immunotherapy, is designed based on tumorigenic antigen, and works to stimulate cytotoxic immune responses against the tumour cells bearing the same antigen in an individual. Amongst several advantages in using peptide vaccines over other immunotherapies comprise the ease of synthesising, the efficacy in inducing T-cell responses, and the safety as demonstrated in many studies and trials (Slingluff C L, Jr, 2011).

However, existing peptide vaccines have had limited success at inducing clinical tumour regressions, despite reliable induction of T cell responses, there has been concern regarding antigenic heterogeneity and antigen loss which limit the efficacy of a single antigen peptide vaccine. Thus, in order to improve peptide vaccine successes in HNSCC, a broader immune response, especially one which can respond to multiple antigens, should be adapted.

Yoshitake et al. 2015 reports that there is an indication that there is indeed a benefit when multi-antigenic vaccines are used simultaneously in HNSCC, as patient survival was prolonged by 1.4 months from 3.5 months to 4.9 months compared to patients who only received standard therapy. Additionally, vaccinated patients who develop cytotoxic T lymphocytes (CTL) responses have a longer overall survival compared to those with negative CTL responses. Again, this strongly indicates that peptide vaccines, particularly multi-antigen peptide vaccines, are able to boost the patient immune response against tumour cells by eliciting a cytotoxic killing effect on the tumour cells.

However, the development of multi-antigen peptide vaccines is not an easy feat due to interference. Major histocompatibility complex (MHC) molecules are essential for the acquired immune system to recognise foreign molecules, and work to bind to antigens derived from pathogens on cell surfaces for recognition by the appropriate T cells. When multi-antigen peptide vaccines are co-administered, the peptides of the vaccine which bind to the same MHC molecule may interfere with one another, as binding of lower-affinity peptides to MHC molecules are competitively inhibited by higher affinity peptides. It has since been suggested to administer these vaccines to different parts of the body to reduce the chances of interference happening. This approach is nevertheless impractical, especially when there is an increase in the number of peptides being administered to the patient.

This fact notwithstanding, the inventors of the present application have successfully been able to demonstrate the immunogenicity and efficacy of a dual-antigen peptide composition, henceforth referred to as PV1, in inducing anti-tumour responses in vitro using peripheral blood mononuclear cells (PBMC) collected from oral and nasopharyngeal carcinoma subjects, and in an animal model. Particularly, PV1 comprises at least two peptides which are able to bind with MHC class I molecules to induce an anti-cancer immune response in a subject. The at least two peptides comprise peptides derived from Four-jointed Box 1 (FJX1) and Melanoma antigen family D4b (MAGED4b).

It will be appreciated that the term "FJX1" or "F1 peptide" refer to the gene, RNA product, or protein product and may be used interchangeably.

It will further be appreciated that the terms "MAGED4b" or "M6 peptide" refer to the gene, RNA product, or protein product, and may be used interchangeably.

It will also be appreciated that the terms "PV1", "PV1 composition", and "PV1 peptides" refers to the combination of M6 and F1 DNA, RNA or protein products and may be used interchangeably.

During the development of this multi-antigen peptide composition, the pattern of MAGED4b and FJX1 expression among oral and nasopharyngeal carcinoma subjects were first identified. Tissue microarray consisting of HNSCC tumour samples were obtained and the expression level of FJX1 and MAGED4b were determined using an immunohistochemistry (IHC) method by probing tissue slides with anti-MAGED4b and anti-FJX1 antibodies.

The expression levels of FJX1 and MAGED4b measured in HNSCC tumour samples are shown below:

TABLE 1

Percentage of subjects shown to express MAGED4b or FJX1 or both

|  | Single MAGED4B | Single FJX1 | Either MAGED4B/ FJX1 | Both MAGED4B & FJX1 | Negative for both |
|---|---|---|---|---|---|
| OSCC (n = 41) | 41 (100.0%) | 40 (97.6%) | 41 (100.0%) | 40 (97.6%) | 0 (0.0%) |
| NPC (n = 53) | 48 (90.5%) | 45 (84.9%) | 48 (90.5%) | 45 (84.9%) | 5 (9.4%) |
| Total (n = 94) | 89 (94.7%) | 85 (90.4%) | 89 (94.7%) | 85 (90.4%) | 5 (5.3%) |

As seen in the table above, the tumour tissue samples of almost all the subjects (94.7%), whether obtained from subjects with oral carcinoma (OSCC) or subjects with nasopharyngeal carcinoma (NPC) indicated that MAGED4b or FJX1 was expressed. Of the 94 tissues collected, only 5 NPC tissues showed no expression of either FJX1 or MAGED4b. 100% of subjects with OSCC expressed FJX1 or MAGED4b.

The expression of MAGED4b and FJX1 in HNSCC samples is further illustrated in FIG. 1, which illustrates the expression of MAGED4b and FJX1 in HNSCC tumour tissue samples. Immunoreactivity of the antibodies against MAGED4b and FJX1 were scored based on percentage of tumour cells with positive staining; a 4-point intensity scoring system, ranging from an intensity of 0 (negative), an intensity of 1 (weak), and intensities of 2-3 (strong), which is depicted in FIG. 1(a). FIG. 1(b) reflects that FJX1 and MAGED4b was found by the inventors to be expressed in more than 80% in both early and late stage OSCC and NPC tumour samples.

It has been discussed in Malaysian patent no. MY-148542-A and Malaysian patent application no. PI 2011003259 (both filed by the inventors) that FJX1 was shown to be expressed in nasopharyngeal carcinoma patients and MAGED4b to be expressed in oral carcinoma patients respectively.

However, it should be highlighted that the difficulty with multi-antigen peptide compositions, which has already been discussed above, is that interference is likely to happen as these peptides may compete against each other to bind to the MHC molecules, thus rendering the efficacy of the peptide composition ineffective. Despite this, it will be successfully shown that the combination of F1 and M6 peptides in the disclosed PV1 composition does the opposite and in fact increases the efficacy of the peptide composition, which will be elaborated below.

PV1 comprises peptides derived from FJX1 and MAGED4b, with amino acid sequences as listed in Table 2 and 3 below. Apart from determining the compatibility of the combination of peptides, it was also imperative that the peptides were able to bind with the MHC class I molecules in order to induce an anti-cancer immune response.

TABLE 2

Peptide sequence of F1

| SEQ ID NO. | Peptide Sequences | Specificity to HLA-type |
|---|---|---|
| 1 | WLLALGSLLAL | HLA-A2 |

TABLE 3

Peptide sequence of M6

| SEQ ID NO. | Peptide Sequences | Specificity to HLA-type |
|---|---|---|
| 2 | RLSLLLVIL | HLA-A2 |

It will be appreciated that in accordance with the present application, the structure of the peptide sequences of FJX1 and MAGD4b may be modified or altered, the modification or alteration comprising deletion, substitution, or insertion of an amino acid in the peptide sequences.

As both FJX1 and MAGED4b are designed based on human leukocyte antigen A2 (HLA-A2) epitope, only subjects with blood samples with matching HLA subtype were used by the inventors. HLA-A2 typing was conducted by staining PBMC samples using phycoerythrin (PE)-tagged anti-HLA-A2 antibodies, and analysed on a flow cytometer.

To maintain the accuracy of this study, a positive control, a HLA-A2 restricted FluM-derived peptide, and a HLA-A2 restricted Human Immunodeficiency Virus (HIV) peptide as an irrelevant peptide control was included. The amino acid sequences of both controls are as shown below:

TABLE 4

Peptide sequence of HLA-A2 restricted FluM-derived peptide

| SEQ ID NO. | Peptide Sequences | Specificity to HLA-type |
|---|---|---|
| 3 | GILGFVFTL | HLA-A2 |

TABLE 5

Peptide sequence of HIV peptide

| SEQ ID NO. | Peptide Sequences | Specificity to HLA-type |
|---|---|---|
| 4 | SLYNTYATL | HLA-A2 |

The purity of the peptides was determined using high performance liquid chromatography (HPLC), all of which were above 80%.

According to the present invention, the peptides may be synthetically prepared or isolated from natural sources, such as native tumours or pathogenic organisms.

In determining the immunogenicity of PV1, the presence of endogenous FJX1- and MAGED4b-specific CD8+ T cells in the isolated PBMCs were first tested using F1, M6, and PV1 peptides, with FluM and HIV peptides used as positive and irrelevant peptide controls respectively, in a dimer assay.

Peptide specific dimers were first prepared by incubating a mixture of dimeric human HLA-A2:Ig fusion protein, β2-microglobulin and peptides (F1, M6, PV1, FluM, or HIV) overnight. The next day, freshly isolated PBMCs were added to the prepared dimers and incubated, before being washed with phosphate buffered saline (PBS). The PBMCs were then re-suspended in PBS and stained with fluorescein isothiocyanate (FITC) tagged anti-IgG1, PE tagged anti-CD8, and allophycocyanin (APC) tagged anti-TCRα/β antibodies. The PBMCs were then washed and re-suspended in PBS and subjected to flow cytometry analysis, where the presence of peptide specific $CD8^+$ T cells was determined by PBMCs that were assessed to be positively stained by IgG1-FITC, CD8-PE, and TCRα/β-APC antibodies. The percentage of $CD8^+$ T cells specific for a given peptide was calculated as the value of peptide dimer-positive $CD8^+$ T cells after subtracting the value obtained for staining without the peptides.

Figure 2:
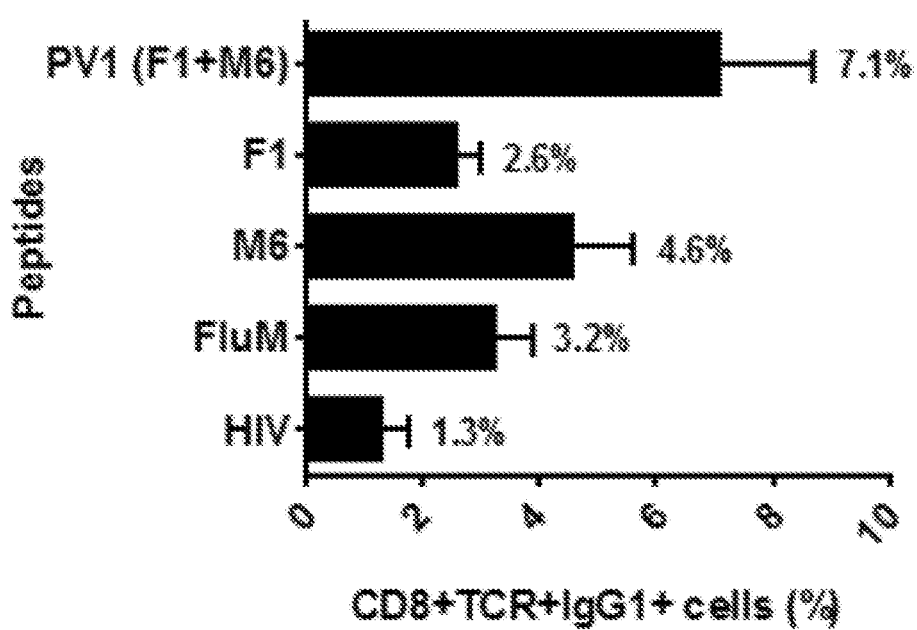
FIG. 2 illustrates the population of peptide-specific T cells in HNSCC patients. The average population of antigen-specific T cells that recognize the peptide-loaded dimers (CD8, TCR and IgG1 positive T lymphocytes) is shown after subtracting non-peptide loaded control. Dimer proteins loaded with FJX1 (F1), MAGED4b (M6) and PV1 (M6 and F1) peptides can be recognized by the inherent T cells from HNSCC patients.

As seen in FIG. 2, the average population of antigen-specific T cells that recognise the peptide-loaded dimers after subtracting non-peptide loaded control is shown. Dimer proteins loaded with F1, M6, and PV1 peptides can be recognised by the inherent T cells from HNSCC subjects, with the 7.1% of T-cells recognizing PV1 peptides, the highest population of T cells compared to single peptides M6 or F1 alone. This therefore indicates that PV1 has a stronger immunogenicity when both peptides are used in combination.

Then, ex vivo and cytotoxic Enzyme-Linked Immuno-Spot (ELISPOT) assays were used to evaluate the presence of interferon gamma (IFNγ) and granzyme B cytokines secreting T cells at a single cell level, and to study the response of peptide-pulsed CTLs derived from the patients to the target cell lines overexpressing the target antigens respectively.

During the ex vivo ELISPOT assay, PBMCs were incubated with interleukin 7 (IL-7) and interleukin 12 (IL-12) proteins in culture medium before washing the PBMCs with salt solution and re-suspending it in complete culture medium. Then, the suspended cells were mixed with F1, M6, PV1, FluM, and HIV peptides respectively and incubated in anti-human IFNγ and granzyme B coated ELISPOT plates. The ELISPOT assay was then performed with slight modifications from manufacturer's instruction. Specifically, the suspended cells were placed on the respective ELISPOT plate for overnight to capture the cytokine released. IFNγ and granzyme B detection antibodies were diluted in PBS containing human AB serum and incubated in each respective plate the next day. This was followed by washing and adding diluted streptavidin tagged secondary antibodies and further incubating the plates. Nitro-blue tetrazolium and 5-bromo-4-chloro-3'-indolylphosphate (BCIP/NBT) plus substrate was then added to visualise spots formed by cytokine secreting T cells. Finally, the detected spots were quantified and analysed, where peptide-specific CTLs were calculated by subtracting spots formed in the background control wells with no exposure to peptide, and where FluM and HIV peptides were used as positive and irrelevant peptide controls respectively.

The cytotoxic ELISPOT assay was used to study the response of peptide-pulsed CTLs derived from the patients to target cell lines overexpressing the target antigens. CTLs were co-cultured with target cells, where this culture was re-suspended in complete culture media supplemented with IL-7 and interleukin 2 (IL-2) proteins and applied to IFNγ and granzyme B ELISPOT plates. The cell suspension was further incubated to allow the interaction between CTLs and target cell line before determining the potential killing ability of CTLs against FJX1 and MAGED4b expressing target cells.

Figure 3:
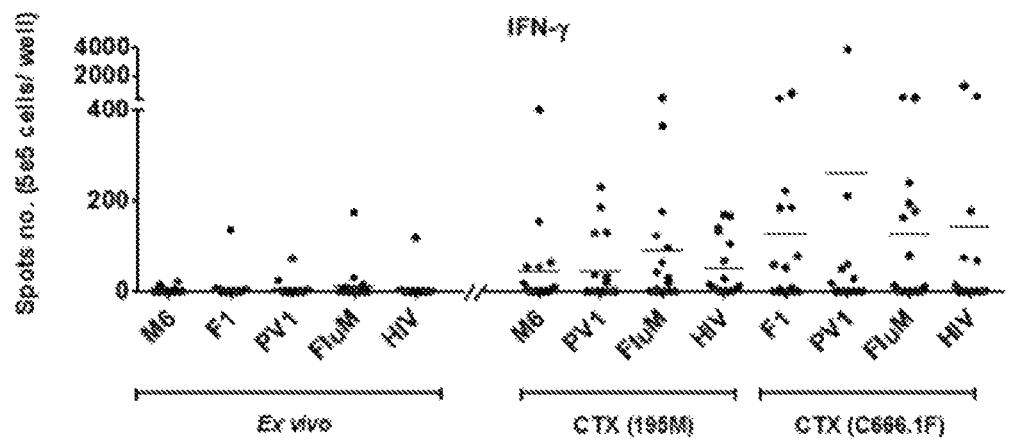
FIG. 3 illustrates that higher levels of cytokine is secreted in HNSCC patients after in vitro stimulation with PV1 peptides.
Figure 3:
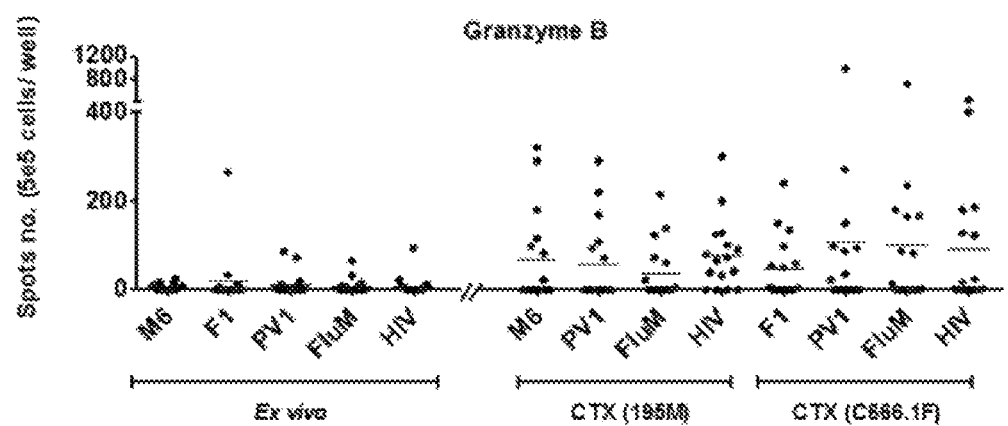

It can be seen from FIG. 3 that higher levels of cytokine is secreted in HNSCC patients after in vitro stimulation with PV1 peptides. The graphs in FIGS. 3(a) and 3(b) show that the secretion of IFNγ and Granzyme B in ex vivo and cytotoxic (CTX) ELISPOT assays. Prior to peptide stimulation, inherent T cell response against M6, F1 and PV1 is low. After the T cells are stimulated by peptide-pulsed dendritic cells, cytotoxic ELISPOT results showed that PV1 induces comparable or better cytotoxic T cell response against target cells (195M and C666.1F), secreting higher levels of IFNγ and granzyme B.

It was also discovered that patients with tumours which overexpressed MAGED4b and/or FJX1 respond better after PV1 stimulation compared to those weakly expressing the MAGED4b and/or FJX1, indicating the specificity of PV1.

Figure 4:
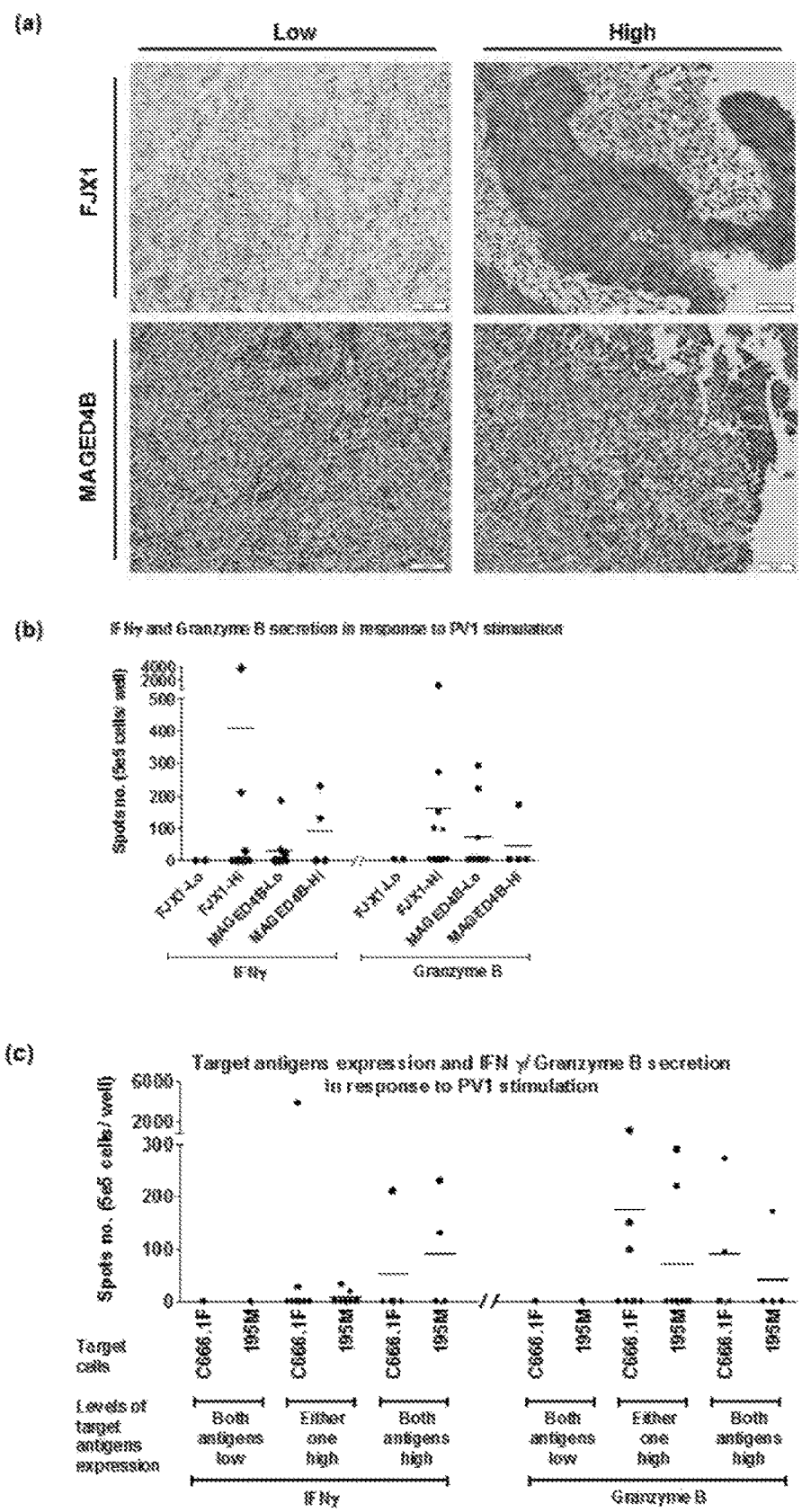
FIG. 4 illustrates the efficacy of PV1 peptides in eliciting T-cell responses in patients who express different expression levels of FJX1 and MAGED4b.

To elaborate further, FIG. 4 indicates 4 groups of subjects based on the intensity of FJX1 and MAGED4b stains of their tumour tissues. FIG. 4(a) illustrates representative images of different expression levels of FJX1 and MAGED4b in staining patients' tumour samples. It can be seen in FIG. 4(b) that patients with express a high level of FJX1 or MAGED4b in their tumours have better response when stimulated with PV1, and secrete higher levels of granzyme B and IFNγ in the cytotoxic ELISPOT assay, compared to patients with low expression of these proteins. Further, it can also be seen in FIG. 4(c) that patients expressing high level of both antigens have a better response towards target cells after being stimulated with PV1, while patients who express low levels for both antigens do not respond to the stimulation, suggesting the specificity of PV1 peptide vaccine To evaluate if the peptides cause any cellular toxicity or non-specific inflammatory responses, a Griess assay for measuring inflammation response by macrophages was first used to assess the levels of inflammation induced by M6 and F1 peptides. Mouse macrophages were treated with various concentrations of M6, F1, and PV1 peptides. Dimethyl sulfoxide (DMSO) in PBS was used as a negative control, whilst LPS was used as a positive control. The degree of inflammation was indirectly measured based on the levels of inducible nitric oxide synthase (iNOS) produced by the mouse macrophage.

Figure 5:
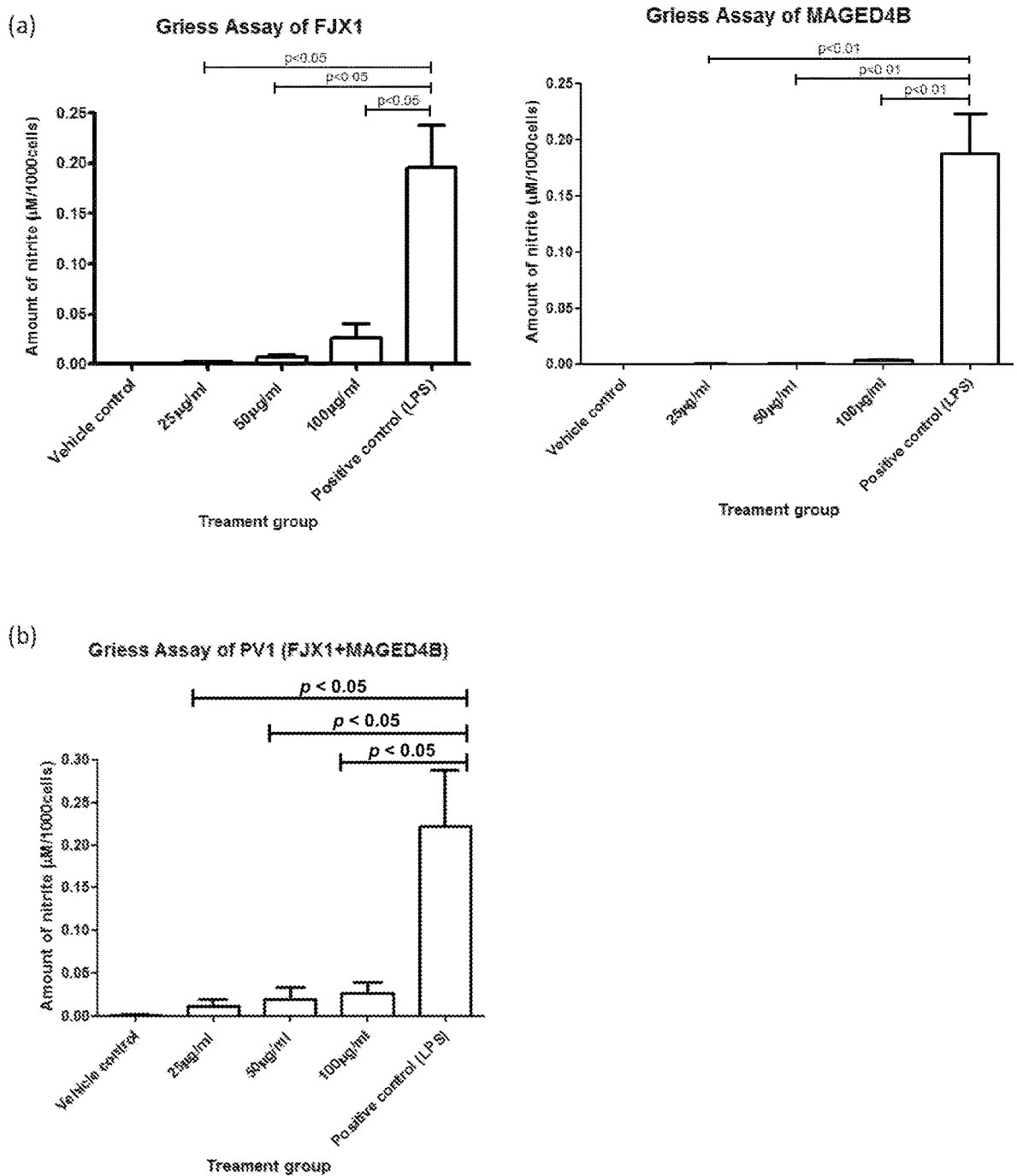
FIG. 5 shows that M6, F1, and PV1 peptides did not increased excessive non-specific inflammation responses by macrophages when compared to lipopolysaccharide (LPS) measured by a Griess assay.

FIG. 5(a) shows the degree of inflammation induced by M6 or F1 peptides on the mouse macrophage. It can be seen that the production of nitrite by the mouse macrophage in the presence of M6 peptide was lower than mouse macrophage which received the LPS stimulation by a 7-fold, regardless of the concentration of M6 peptide administered. Similarly, this can also be observed in mouse macrophage in the presence of F1 peptide, where the amount of nitrite release is 10-fold lower than that of the positive control (LPS). Given the low production of nitrite by the M6 and F1 peptides, it can therefore be suggested that the upregulation of iNOS expression is not stimulated by said peptides, subsequently indicating that the degree of inflammation induced by the M6 and F1 peptides were low and is not expected to cause undesirable effect by inducing non-antigen-specific responses Consistent results were shown when the M6 and F1 peptide were combined as the PV1 peptide, where the amount of iNOS accumulation was significantly lower than those in the LPS treatment group, as seen in FIG. 5(b).

Then, further assessments were run to determine the evaluation of the PV1 composition in an animal model.

Armed with the results obtained from the dimer and ELISPOT assay using patient PBMCs, the immunogenicity and efficacy of PV1 were evaluated using a transgenic mouse model, which enables the modelling of human T-cell immune responses to HLA-A2 presented antigens.

Mice were vaccinated with 6 different treatment groups as seen in the table below:

TABLE 6

Treatment groups of vaccinated mice

| Groups | Treatment |
| --- | --- |
| Group 1: | 5% DMSO |
| Group 2: | IFA |
| Group 3: | 100 μg PV1 + IFA |
| Group 4: | 500 μg PV1 + IFA |
| Group 5: | 1000 μg PV1 + IFA |
| Group 6: | 2000 μg PV1 + IFA | where DMSO is dimethyl sulfoxide, PV1 is a composition comprising of M6 and F1 peptides, and IFA is Incomplete Freund's adjuvant.

After the vaccination period, the mice were euthanized and the immune cells were harvested from the mice spleen. The presence of IFNγ-secreting peptide specific CD8$^+$ T cells of vaccinated mice was determined using a dimer assay and compared against the results of the vehicle control group.

Then, using an ELISPOT assay, the population of T-cells capable of carrying out cytotoxic function to kill cancer cells presenting the peptides post-vaccination was evaluated.

Figure 6:
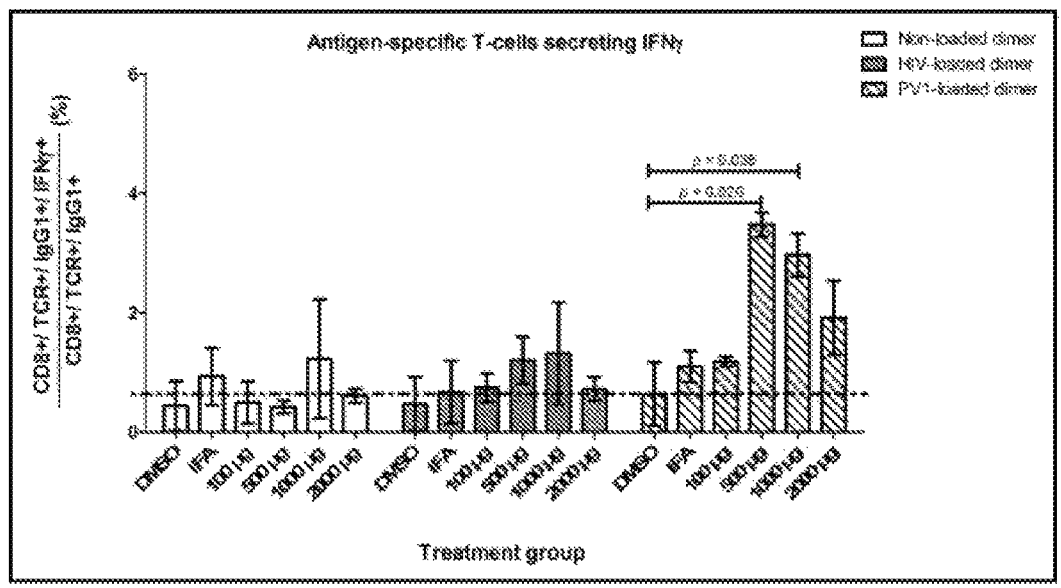
FIG. 6 shows the immunogenicity of the PV1 peptide when tested in mice.
Figure 6:
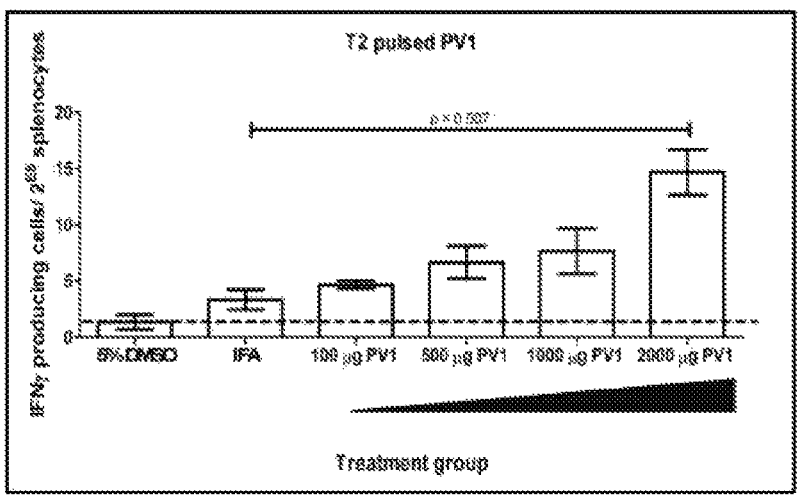

As seen in FIG. 6($a$), mice vaccinated with a concentration as low as 500 μg of PV1 were able to demonstrate a high recognition towards PV1 loaded dimers, compared to the vehicle control mice. This response is peptide specific as the vaccinated mice showed a baseline or negligible response when exposed to non-loaded and irrelevant peptide (HIV) loaded dimers.

In addition, the inherent T cells from vaccinated mice were also able to recognise T2 cells presenting the PV1 peptides, and were able to execute killing activities against these T2 cells at dose dependent manners in the ex vivo ELISPOT assay as seen in FIG. 6($b$). Again, this indicates and encourages the suggestion that the PV1 vaccination may increase PV1 recognising T cells in these mice.

Figure 7:
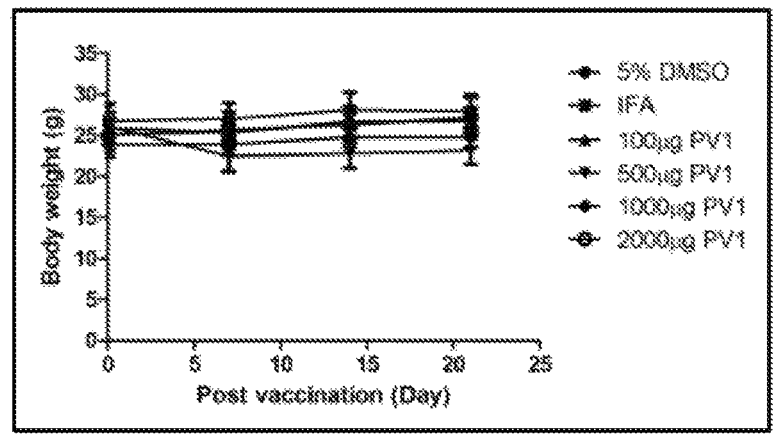
FIG. 7, (a) illustrates the body weight of the vaccinated mice during the vaccinated period and (b) shows images of major organs (heart, lungs, kidney, liver, and spleen) of the vaccinated mice.
Figure 7:
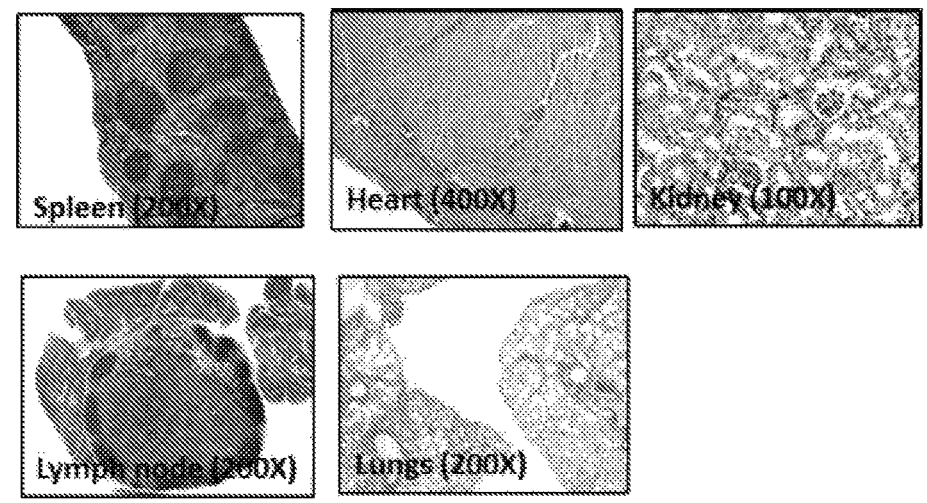

Advantageously, it should be noted that throughout the vaccination period, mice weight were taken once a week. No weight loss or adverse events during this period were observed. Additionally, major organs such as the heart, lungs, kidney, liver, or spleen were harvested from the mice from all PV1 administered treatment groups, where no local toxicity was observed in these mice. This is further illustrated in FIGS. 7($a$) and ($b$).

Since a concentration of 500 μg of PV1 was able to stimulate T cell recognition towards PV1 in the immunogenicity test, 1000 μg was chosen to be tested in the subsequent assessment to determine the efficacy of PV1 in delaying tumour growth. A total of 1×10$^6$ of syngeneic B16 melanoma cells expressing human HLA-A2 (AAD) and MAGED4b genes were transplanted into mice subcutaneously. After the tumour size reached 30-50 mm$^3$, the mice were randomly assigned to two treatment groups. The first group received 1000 μg of PV1 peptides with Incomplete Freund's Adjuvant (IFA), while the vehicle control group received 5% DMSO in PBS. The tumour size was measured twice weekly.

Figure 8:
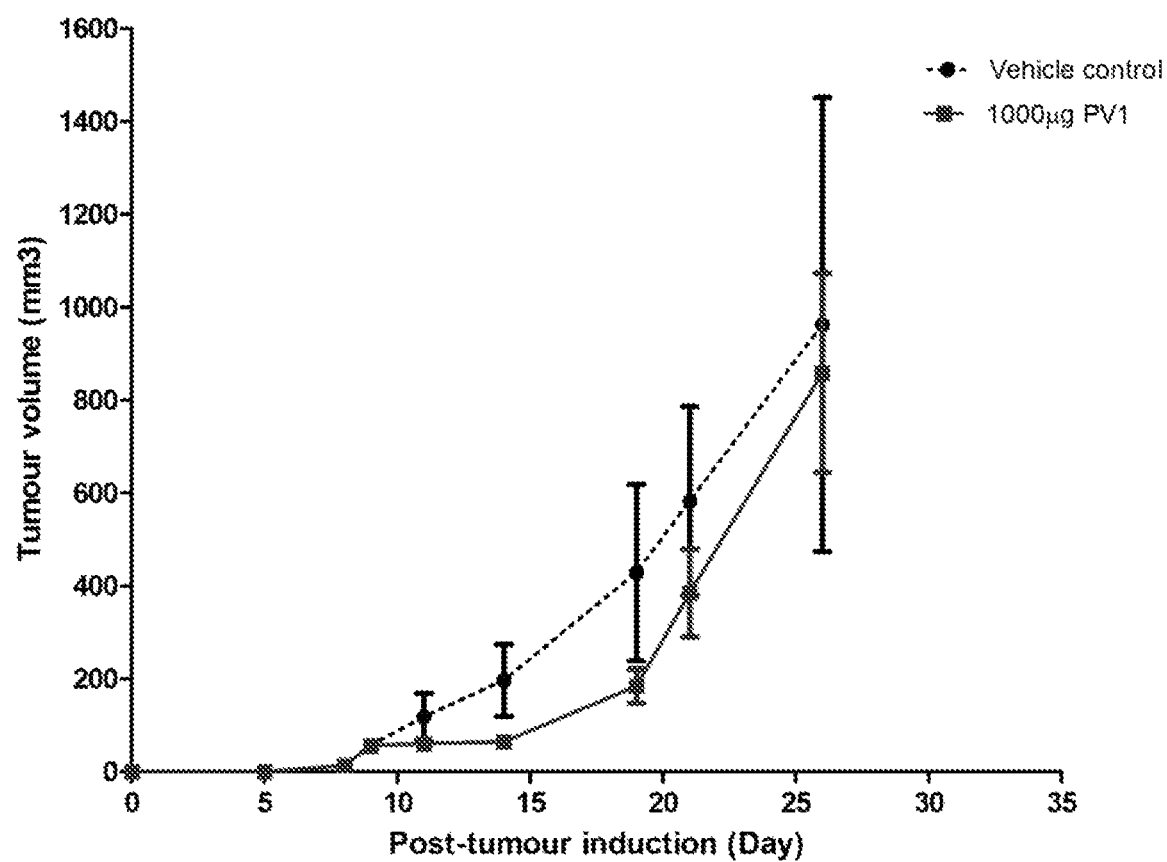
FIG. 8 indicates the tumour growth of mice vaccinated with PV1 peptides compared with a vehicle control.

As illustrated in FIG. 8, it can be seen that mice treated with PV1 and adjuvant showed a delay in tumour growth in comparison to the vehicle control group. This therefore indicates that PV1 is able to delay tumour growth.

Based on the results above, PV1 strongly indicates that it is efficient in delaying the growth of the tumour with negligible, if any, adverse effects on the major organs of the vaccinated mice.

The PV1 peptide vaccine has demonstrated to be immunogenic both in vitro and in vivo. Most importantly, the use of PV1 has exhibited antigen-specific cytotoxicity against target cancer cell line expressing MAGED4b and FJX1 in vitro and delayed tumour growth in vivo, suggesting the potential of PV1 as therapeutic vaccine candidate for HNSCC Beneficially, PV1 could benefit not only HNSCC patients, but also those suffering from breast, colon, lung, prostate, and rectum cancers. In table 7 below, the inventors show that MAGED4b and FJX1 are also expressed in tumour tissues of patients with breast, colon, lung, prostate, and rectum cancers.

TABLE 7

Percentage of patients shown to express MAGED4b or FJX1 or both, and the level of expression of each protein (a)

|  | MAGED4B | | | FJX1 | | |
| --- | --- | --- | --- | --- | --- | --- |
|  | Negative | Low | High | Negative | Low | High |
| OSCC | 0/49 (0.0%) | 12/49 (4.1%) | 37/49 (75.5%) | 2/49 (2.0%) | 11/49 (22.4%) | 36/49 (73.5%) |
| NPC | 5/63 (7.9%) | 5/63 (7.9%) | 53/63 (84.1%) | 10/74 (13.5%) | 11/74 (14.8%) | 53/74 (71.6%) |
| Total | 5/112 (4.5%) | 17/112 (15.2%) | 90/112 (80.4%) | 12/123 (9.8%) | 22/123 (17.9%) | 89/123 (72.4%) |

(b)

|  | MAGED4B | FJX1 | Either MAGED4B/FJX1 | Both MAGED4B & FJX1 | Both negative |
| --- | --- | --- | --- | --- | --- |
| OSCC (n = 41) | 41 (100.0%) | 40 (97.6%) | 41 (100.0%) | 40 (97.6%) | 0 (0.0%) |
| NPC (n = 53) | 48 (90.5%) | 45 (84.9%) | 48 (90.5%) | 45 (84.9%) | 5 (9.4%) |
| Total (n = 94) | 89 (94.7%) | 85 (90.4%) | 89 (94.7%) | 85 (90.4%) | 5 (5.3%) |

TABLE 7-continued

Percentage of patients shown to express MAGED4b or FJX1 or both, and the level of expression of each protein (c)

| Cancer type | MAGED4B | | | FJX1 | | |
|---|---|---|---|---|---|---|
| | Negative | Low | High | Negative | Low | High |
| Breast | 0/41 (0.0%) | 7/41 (17.1%) | 34/41 (82.9%) | 5/41 (12.2%) | 11/41 (26.8%) | 25/41 (61.0%) |
| Colon | 5/30 (16.7%) | 8/30 (26.7%) | 17/30 (56.7%) | 15/30 (50.0%) | 5/30 (16.7%) | 10/30 (33.3%) |
| Lung | 0/42 (0.0%) | 17/42 (40.5%) | 25/42 (59.5%) | 11/48 (22.9%) | 19/48 (39.6%) | 18/48 (37.5%) |
| Prostate | 8/42 (19.0%) | 14/42 (33.3%) | 20/42 (47.5%) | 7/44 (15.9%) | 11/44 (25.0%) | 26/44 (59.1%) |
| Rectum | 3/16 (18.8%) | 2/16 (12.5%) | 11/16 (68.8%) | 2/14 (14.3%) | 7/14 (50.0%) | 5/14 (35.7%) |
| Total | 16/171 (9.4%) | 48/171 (28.1%) | 107/171 (62.6%) | 40/177 (22.6%) | 53/177 (29.9%) | 84/177 (47.5%) |

(d)

| Cancer type | MAGED4B | FJX1 | Either MAGED48/FJX1 | Both MAGED4B & FJX1 | Both negative |
|---|---|---|---|---|---|
| Breast | 41/41(200.0%) | 36/41 (87.8%) | 41/41 (100.0%) | 36/41 (87.8%) | 0/41 (0.0%) |
| Colon | 25/30 (83.3%) | 15/30 (50.0%) | 27/29 (93.1%) | 11/29 (87.9%) | 2/29 (6.9%) |
| Lung | 42/42 (100.0%) | 37/48 (77.1%) | 42/42 (100.0%) | 32/42 (76.2%) | 0/42 (0.0%) |
| Prostate | 34/42 (81.0%) | 37/44 (84.1%) | 38/40 (95.0%) | 29/40 (72.5%) | 2/40 (5.0%) |
| Rectum | 13/16 (81.2%) | 12/14 (85.7%) | 13/14 (92.9%) | 11/14 (78.6%) | 1/14 (7.11%) |
| Total | 155/171 (90.5%) | 137/177 (77.4%) | 161/166 (97.0%) | 119/166 (71.7%) | 5/166 (3.0%) |

(e)

| Cancer type | MAGED4B | | FJX1 | |
|---|---|---|---|---|
| | Early | Late | Early | Late |
| Breast | 28/28 (100.0%) | 13/13 (100.0%) | 25/28 (89.3%) | 11/13 (84.6%) |
| Colon | 20/23 (87.0%) | 5/7 (71.4%)) | 12/23 (52.2%) | 3/7 (42.9%) |
| Lung | 40/40 (100.0%) | 2/2 (100.0%) | 35/46 (76.0%) | 2/2 (100.0%) |
| Prostate | 20/27 (74.1%) | 14/15 (93.3%) | 22/26 (84.6%) | 15/18 (83.3%) |
| Rectum | 10/13 (76.9%) | 3/3 (100.0%) | 9/11 (81.8%) | 3/3 (100.0%) |
| Total | 118/131 (76.3%) | 37/40 (92.5%) | 103/134 (76.9%) | 34/43 (79%) |

It can be seen from Table 7 above that FJX1 and/or MAGED4b are expressed in more than 90% of OSCC and NPC samples. These two antigens were also expressed in tissues of patients with breast, colon, lung, prostate, and rectum cancer. About 97% of subjects with these cancer types were measured to express either MAGED4b or FJX1 [Table 7(d)]. The expression of MAGED4b and FJX1 was detected in both early and late stages tumour of these 5 cancer types (Table 7). Given that both the proteins were highly overexpressed in almost half of these cancer types, this strongly indicates that a peptide composition, comprising FJX1 and MAGED4b may be developed to treat not only HNSCC subjects, but also subjects with breast, colon, lung, prostate, and rectum cancer.

According to the present application, the peptide composition can further be developed into a multi-antigen peptide vaccine. Particularly, a vaccine comprising at least FJX1 and MAGED4b peptides may be developed for inducing the anti-cancer immune response in the subject by binding with MHC Class I molecules. In the preferred embodiment, the MHC class I molecules are HLA-A2 molecules.

The peptide vaccine may be used in combination with any available cancer therapeutic treatments. Taking an immune checkpoint inhibitor as an example, when used alone the immune checkpoint inhibitor may not be sufficient in reactivating a patient's immune system. However, when used in combination with PV1, an approach to increase the repertoire of antigen specific T cells, is believed to be capable of further enhance the response rate in HNSCC patients.

However, it will be appreciated that the cancer therapeutic treatment is not limited to immune checkpoint inhibitors alone, and may comprise other cancer therapeutic treatments.

Additionally, adjuvants may also be administered in combination with PV1 and the cancer therapeutic treatment selected to increase immune response to PV1. An example of an adjuvant such as Freund's adjuvant or human granulocyte macrophage colony-stimulating factor (GM-CSF) may be useful.

Alternatively, the peptide composition can also be used in the manufacture of a medicament. Particularly, an effective amount of FJX1 and MAGED4b can be used in the manufacture of a medicament for treating any one or a combination of HNSCC, breast cancer, colon cancer, rectum cancer, lung cancer, or prostate cancer in a subject in need thereof, wherein the medicament is capable of binding with the MHC Class I molecules to induce an anti-cancer immune response in the subject.

The following examples are included to further disclose the preferred embodiments of the invention. However, it will be appreciated that the techniques as employed in the examples follow represent techniques discovered by the inventors to function well in the practice of the invention, and can thus be considered to constitute preferred modes for its practice. However, those skilled in the art may adapt changes in the specific embodiments which are disclosed and may still obtain a like or similar result without departing from the scope of the invention.

Example 1

Materials and Methods
Patient Samples

Newly diagnosed HNSCC patients from 4 referral hospitals in Malaysia (Penang General Hospital, Penang, Tengku Ampuan Rahimah Hospital, Selangor, University of Malaya Hospital, Kuala Lumpur, and Tung Shin Hospital, Kuala Lumpur) were enrolled for this study. This project was approved by the Institutional Review Board, Faculty of Dentistry, University of Malaya [reference: DF OS0910/0049(L)], and the Medical Research and Ethics Committee, Ministry of Health, Malaysia (NMRR-09-944-4848).

The purpose of the study was explained to all patients, with written informed consent obtained prior to collection of the blood samples.

The blood samples were processed to determine the HLA molecule type of each of the patients, which will be described in detail herein below. The demographic information of all patients is shown in Table 8 below.

TABLE 8

Summary of recruited HLA-A2 patients' clinical characteristics

| Variables | Sample size, n (%) |
|---|---|
| Disease | |
| Nasopharyngeal cancer | 16 (80.0) |
| Oral cancer | 4 (20.0) |
| Age (median, 48.5; range, 30-67) | |
| ≤40 | 3 (15.0) |
| ≥40 | 17 (85.0) |
| Ethnicity | |
| Chinese | 16 (80.0) |
| Malay | 2 (10.0) |
| Indian | 2 (10.0) |
| Gender | |
| Male | 17 (85.0) |
| Female | 3 (15.0) |
| Overall staging | |
| Early stage (Stage I and II) | 4 (20.0) |
| Late stage (Stage III and IV) | 16 (80.0) |

Cell Lines

Oral (ORL-48, ORL-115, ORL-136, ORL-150, ORL-153, ORL-156, ORL-166, ORL-174, ORL-188, ORL-195, ORL-196, ORL-204, ORL-207, ORL-214, ORL-215, ORL-247), nasopharyngeal (NP69, NP640, HK1, TW01, C666.1, HeLa/S and HeLa/T), breast (MCF-7 and SKBR-3), colon (HT-29 and HCT-116), prostate (PC-3), lung (A549) cancer cell lines, four normal oral keratinocyte primary cultures (ORL-231, ORL-295, ORL-235, ORL-232) and two immortalised nasopharynx (NP) cell lines, NP69 and NP460 were used by the inventors. The HeLa/S and HeLa/T were a variant of HeLa cells that were previously mistaken as NPC cell lines (Ye et al. 2015). These cell lines were purchased (Gibco, Thermo Fisher, MA, USA) and cultured in recommended media (DMEM/F12 for oral cancer cell lines; RPMI-1640 for nasopharyngeal, breast, colon and lung cancer cell lines) and supplemented with 2 mM L-glutamine (Sigma Aldrich, MO, USA) and 10% fetal bovine serum (Gibco, Thermo Fisher, MA, USA). Whereas, Keratinocyte-SFM (Gibco, Thermo Fisher, MA, USA) was used to culture normal oral keratinocyte and non-malignant nasopharynx cell lines. Cell lines overexpressing target antigens, ORL195-MAGED4B (referred as 195M) and HeLa/T-FJX1 (referred as HeLa/T-F), were used as positive controls in western blot experiments. C666.1-A2 cell line (as provided by Dr. Ricardo Dolcetti, Centro di Riferimento Oncologico, Italy) overexpressing FJX1 (referred as C666.1F); and ORL-195 overexpressing MAGED4B (referred as 195M) were used as target cell lines in cytotoxic ELISPOT assay which will described more below. All cell lines used in this study has been authenticated prior to their use in this study.

Peptides

The peptides utilised in this example comprises of two HLA-A2 restricted peptides derived from FJX1 (F1) and MAGED4b (M6). HLA-A2-restricted FluM-derived peptide was used as a positive control and a HIV peptide was used as an irrelevant peptide control. The sequences of the peptides are as shown in Tables 2-5. AH peptides used for this study were produced commercially by JPT Peptide Technologies (Berlin, Germany). The purity of the peptides was determined and ensured through the use of HPLC, wherein the purity results of the peptides were above 80%.

Quantitative PCR (qPCR)

Quantitative PCR (qPCR) was used to determine the mRNA level of the two target antigens, the M6 and F1 antigens, in OSCC and NPC cell lines. Total RNA from all of the 16 OSCC and 7 NPC cell lines were extracted using the Nucleospin RNA II Purification Kit (Macherey-Nagel, Düren, Germany) and used to synthesis cDNA using oligo (dT) primer and Superscript II (Invitrogen, Thermo Fisher, MA, USA). Quantitative PCR was performed with standard SYBR Green protocol using ABI Prism 7500® Sequence Detection System (Applied Biosystems, Germany). Glyceraldehyde 3-phosphate dehydrogenase (GAPDH) was amplified and served as an internal control.

The primers used are as below:

```
FJX1:
sense
5'CCCGCAAAGGTGTCTAAAAACT3'
and antisense
5'GTGCTGGCACAGTAAAGAATCCT3';

MAGED4b:
sense
5'CCAGAATCAGAACCGAGA3'
and antisense
5'CCAAAATCTCCGTCCTCA3';

GAPDH:
sense
5'GAAGGTGAAGGTCGGAGTC3'
and antisense
5' GAAGATGGTGATGGGATT TC 3'.
```

A minimum of 2-fold increase in the relative expression was considered overexpressed when compared to expression levels of normal oral and nasopharynx tissues.

Western Blots

Cells were lysed on ice with RIPA lysis buffer (5% NaDOC, 1% SDS, 25 mM HEPES pH 7.5, 1 M HCl, 1.5 mM $MgCl_2$, 1 mM EDTA, 1% Triton X-100, 1 mM DTT) supplemented with 1×HALT protease inhibitor cocktail (Pierce Biotechnology, IL, USA). Cell lysates were collected after centrifugation at 10000 g for 20 minutes at 4° C. The concentration of total protein was determined using Bradford protein assay (Pierce Biotechnology, MA, USA).

50 μg of total protein was subjected to 12% and 10% SDS-polyacrylamide gel electrophoresis (for the detection of FJX1 and MAGED4b protein respectively) and transferred onto Immobilon-P membrane (Millipore, MA, USA). Blots were blocked with 5% skimmed milk (Tris-buffered saline with 0.1% Tween-20, TBST) for 1 hour and further incubated with the following primary antibodies: anti-MAGED4B (1:1000, Sigma Aldrich, MO, USA), anti-FJX1 (1:2000, Aviva Systems Biology, CA, USA). Blots were washed (×3 for 5 minutes each) in TBS buffer containing 0.1% Tween-20 (TBS-T) and then probed with respective secondary antibodies conjugated with horseradish peroxidase (1:10000; Southern Biotech, AL, USA) for 1 hour. After washing (TBS-T), detection was performed via enhanced chemiluminescence method, using the FluorChem HD2 Imaging System (ProteinSimple, CA USA). The blots were probed with anti-GAPDH (1:1000, Trevigen, MD, USA) or anti-actin (1:1000, Milipore, CA, USA) antibodies as housekeeping control for each experiment.

Immunohistochemistry

Tissue microarray (TMA) slides consisting of NPC (n=74), OSCC (n=49) and 179 multiple cancers (breast, n=41; colon, n=30; lung, n=48; prostate, n=44; rectum, n=16) included in the study were purchased from Biomax (MD, USA). Expression levels of the target proteins were detected by immunohistochemistry (IHC) using anti-MAGED4B (1:100; Cat. no. HPA003554; Sigma Aldrich, MO, USA) and anti-FJX1 (1: 200; Cat. no. HPA059220; Sigma Aldrich MO, USA) antibodies followed the detection system using Dakocytomation Envision+ Dual Link SystemHRP (DAB+) kit (Dako, Glostrup, Denmark). IHC analysis was also performed on the archived FFPE OSCC and NPC tissue sections from the patients enrolled for the PV1 efficacy evaluation. Immunoreactivity of the two antibodies was scored based on percentage of tumour cells with positive staining and a 4-point intensity scoring system: 0=negative expression; 1=weak positive; 2=moderate positive; 3=strong positive (Charafe-Jauffret et al. 2004). All IHC analysis was evaluated by certified pathologist. Tissue microarrays with missing, incomplete cores, or too little tumour to assess were excluded from the analysis.

Preparation of Peripheral Blood Mononuclear Cells (PBMC)

35 ml of blood from OSCC or NPC patients was collected in CPT Vacutainer tubes (Becton Dickinson, USA) and PBMCs were isolated according the instructions of the manufacturer. PBMCs were then washed in Hanks' Balanced Salt Solution (HBSS) (Gibco, Thermo Fisher, MA, USA) and re-suspended in complete culture media containing Roswell Park Memorial Institute (RPMI) media (Gibco, Thermo Fisher, MA, USA) supplemented with 5% heat-inactivated human AB serum (Gemini Bio-Product, CA, USA), 1× penicillin/streptomycin (Gibco, Thermo Fisher, MA, USA) and 2 mM L-glutamine. The isolated PBMCs were then used for HLA typing through the use of a HLA-A2:Ig dimer assay, and ex vivo and cytotoxic ELISPOT assays, which will be described in detail below.

HLA Typing of Blood Specimen

Given that both the FJX1 and MAGED4b peptides are HLA-A2 specific, the inventors only utilised blood samples with the matching HLA subtype. The HLA-A2 status was determined by staining PBMC samples using phycoerythrin (PE) tagged mouse anti-human HLA-A2 antibody (clone BB7.2; BD Pharmingen, CA, USA). PBMCs stained with PE-tagged mouse anti-human HLA IgG2b k-isotype (clone BB7.2; BD Pharmingen, CA, USA) and mouse anti-human HLA-ABC (clone DX17; BD Pharmingen, CA, USA) were used as negative and positive controls respectively. For staining, cells were incubated with the appropriate antibodies at 4° C. for 1 hour, washed, and analysed on a FACSCanto 2 cytometer (BD Biosciences, CA, USA).

Dimer Assay

The presence of endogenous FJX1 and MAGED4b specific CD8$^+$ T cells in PBMCs of HLA-A2 positive NPA and OSCC patients were assessed using the HLA-A2:Ig dimer assay. Peptide specific dimers were prepared by combining 1 μg of recombinant soluble dimeric human HLA-A2:Ig recombinant protein (BD Pharmingen, CA, USA), 0.25 μg of β2-microglobulin (Sigma Aldrich, MO, USA) and 5 μg of peptide (F1, M6, or PV1) and incubated overnight at 37° C. Dimers loaded with complete culture media (CM) and β2-microglobulin were used as background control, dimers loaded with HIV peptide and β2-microglobulin were used as an irrelevant peptide control, and FluM-loaded dimers with β2-microglobulin were used as a positive control. The next day, freshly isolated PBMCs were added to the respective peptide loaded dimers in separate round bottom polypropylene tubes (BD Falcon, CA, USA) and incubated for 30 minutes at 4° C. and washed with 1 ml of phosphate buffered saline (PBS). The cells were then re-suspended in 100 μl of PBS and stained with FITC-conjugated rat anti-mouse IgG1 (clone A85-1; BD Biosciences, CA, USA), PE-conjugated mouse anti-human CD8 (clone HIT8a; BD Biosciences, CA, USA), and APC-conjugated mouse anti-human TCR α/β (clone BW242/412; Miltenyi Biotech, Germany) for 1 hour at 4° C. The cells were then washed and re-suspended in PBS and subjected to flow cytometry analysis using the FACSCanto 2 cytometer (BD Biosciences, CA, USA). The presence of peptide specific CD8$^+$ T cells was determined by cells that were assessed to be positive for IgG1, CD8, and APC, and the percentage of CD8$^+$ T cells specific for a given peptide and calculated as the value of peptide dimer-positive CD8$^+$ T cells after subtracting the value obtained for staining without the peptides.

Ex Vivo ELISPOT

ELISPOT assay was used to evaluate the presence of cytokines (IFNγ and Granzyme B) secreting T cells at a single cell level. As described previously, ex vivo ELISPOT was used to determine the inherent T cells from patient PBMCs that recognized the peptides (Lim et al. 2014). First, PBMCs were incubated with 50 ng/ml of IL-7 and 10 ng/ml of IL-12 in culture medium for two hours at 37° C. After two hours of incubation, the cells were washed with 4 ml of HBSS (Gibco, Thermo Fisher, MA, USA) and re-suspended in 200 μl of complete culture media. The suspended cells were then mixed with 50 μg/ml of F1, M6, PV1, FluM and HIV peptides. Each of the 100 μl of mixture was incubated overnight in the anti-human IFNγ/Granzyme B coated ELISPOT plates (Mabtech, Sweden). After an overnight incubation, the ELISPOT assay was performed according to the manufacturer's instructions with slight modifications. IFNγ or Granzyme B detection antibodies were added into the respective plates and incubated for two hours at 37° C. This was followed by washing and the addition of the streptavidin tagged secondary antibody and the plate was further incubated for 45 minutes at 37° C. Both antibodies were diluted at 1:500 in PBS containing 0.5% human AB serum (Gemini Bio-Products, CA, USA). BCIP/NBT-plus substrate was added to visualize spots formed by cytokine-secreting T cells. The detected spots were then quantitated using CTL ELISPOT Analyzer (Cellular Technology Limited, OH, USA) and analyzed using the ImmunoSpot Professional Software (Cellular Technology Limited, OH, USA). Peptide-specific CTLs were calculated by subtracting spots formed in the background control wells with no exposure to peptide and FluM peptide and HIV peptides were used as positive and irrelevant peptide controls respectively.

Dendritic Cells (DCs) and Cytotoxic T-Lymphocytes (CTLs) Isolation and Culture

Dendritic cells from patients were isolated and subsequently used as antigen presenting cells. Briefly, PBMCs were re-suspended in macrophage-serum free media (M-SFM) (Gibco, Thermo Fisher, MA, USA), seeded in a 6-well plate and incubated for 1 hour at 37° C. After incubation, non-adherent cells from PBMCs were collected, rinsed in HBSS and then re-suspended in complete culture media contained 10 ng/ml IL-7. Approximately 2-5×10⁵ cells per well were seeded into round bottom 96-well plates. Cells were then incubated for 2-5 days at 37° C. for T cell expansion with the addition of 50 µg/ml of peptides. The adherent cells resulting from the incubation, were cultured at 37° C. for 2-5 days in M-SFM in the presence of 100 ng/ml GM-CSF and 25 ng/ml IL-4 to induce differentiation of dendritic cells (DCs). Differentiated DCs were collected from the culture dish by dislodging the cells with media and then aliquoted into 1.5 ml centrifuge tube, incubated with 50 µg/ml peptides (F1, M6 and PV1) for 2 hours at 37° C. before applying to the matured T cells derived from non-adherent PBMCs. After co-culture for 18-24 hours, 10 ng/ml of IL-2 was added to the DCs/T cell culture and incubated for an additional 24 hours. After incubation, culture media containing IL-2 was replaced with fresh complete culture media and further incubated in 37° C. for 3-5 days to allow the activation of cytotoxic T-lymphocytes (CTLs). CTLs were then co-incubated with target cells (195M and C666.1F) in the post-expansion cytotoxic ELISPOT assay to determine the potential killing ability of CTLs against FJX1 or MAGED4b expressing target cells.

Cytotoxic ELISPOT Assay

Cytotoxic ELISPOT assay was used to study the response of peptide-pulsed CTLs derived from the patients to the target cell lines overexpressing the target antigens. CTLs were co-cultured with 195M and C666.1F at an effector to target ratio of 20:1, and this culture was re-suspended in 200 µl of complete culture media supplemented with 20 ng/ml of IL-7 and IL-2 and then applied 100 µl in each well to the IFNγ or Granzyme B ELISPOT plate. Cell suspension was then further incubated in 37° C. for 16 hours. Then, ELISPOT assay was performed as described above.

Results

Patient Demographics

Peripheral blood from 41 HNSCC (NPC and OSCC) patients was collected for use in this study. Of these, ~50% (20/41) were HLA-A2 positive and used for subsequent analysis. Amongst these patients, 16/20 were NPC patients and 4/20 were OSCC patients. 80% (16/20) of these HLA-A2 positive patients are from advanced disease stages (stage III and stage IV) and the demographics of these patients are shown in Table 8. Of the 20 HLA-A2 patients, samples from 15 patients were subjected to the dimer assay while 16 were subjected to the ex vivo and cytotoxic ELISPOT assays. The remaining samples were excluded from the experiments due to either insufficient PBMCs or sub-optimal sample quality (blood lysed).

MAGED4B and FJX1 are Tumour Antigens Overexpressed in HNSCC

Figure 9:
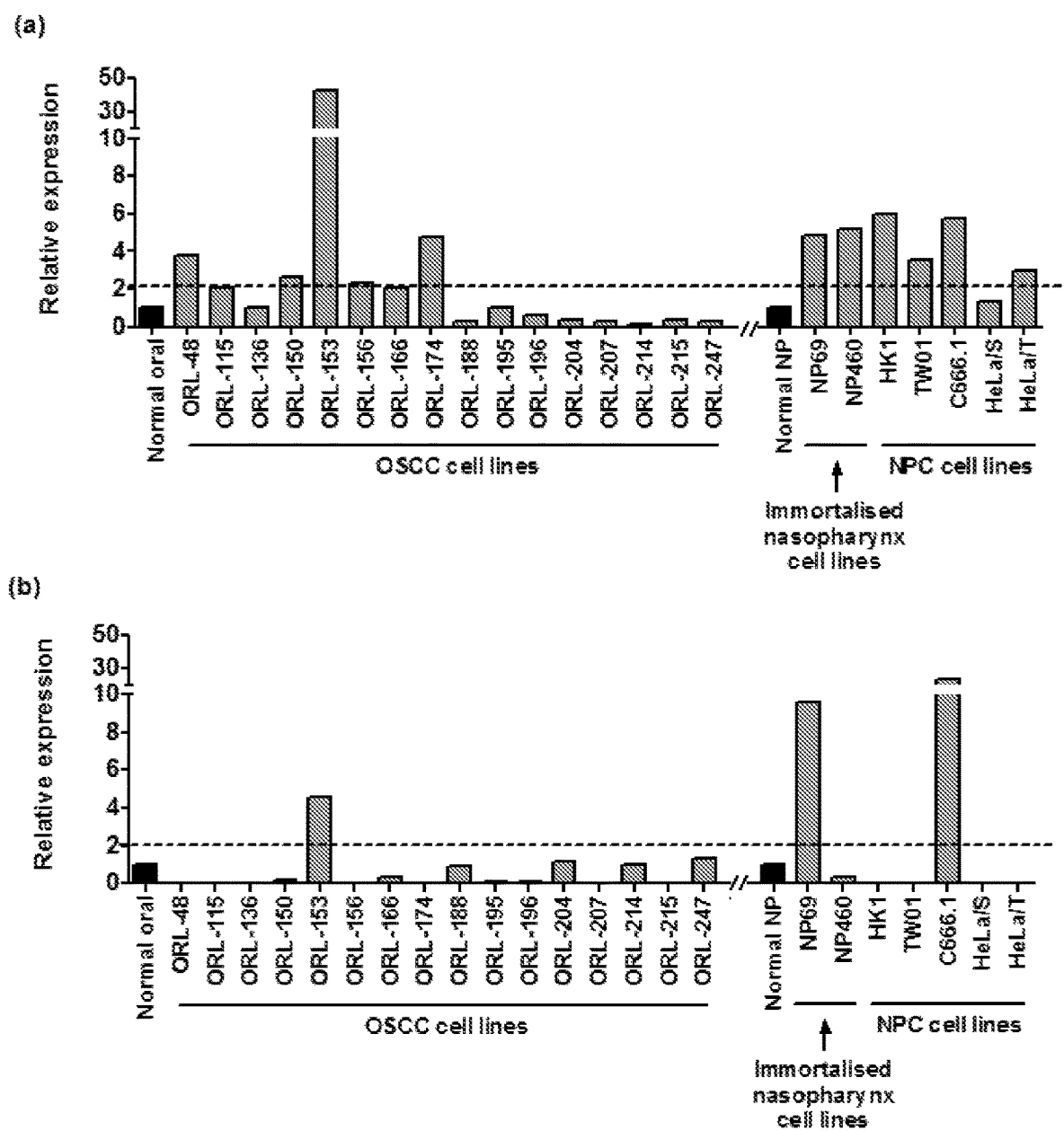
FIG. 9, (a) and (b) show the overexpression of FJX1 and MAGED4b protein at mRNA levels in OSCC and NPC cell lines respectively.
Figure 10:
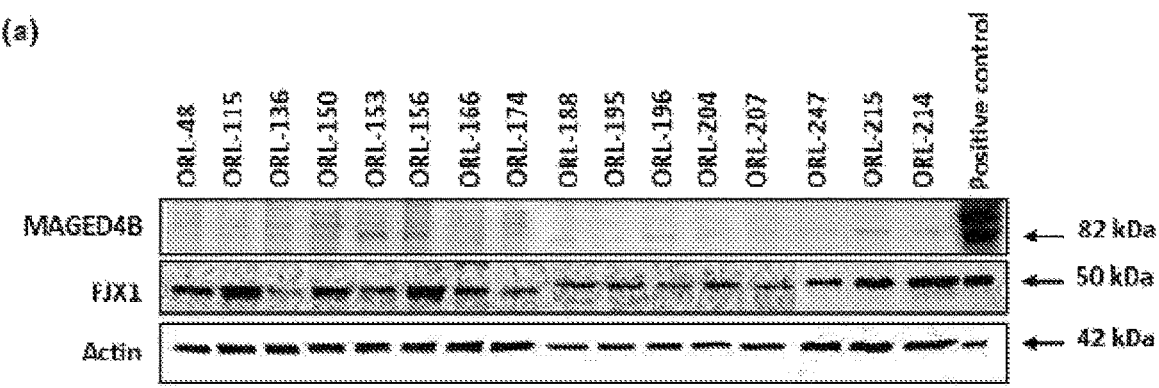
FIG. 10 indicates the expression of MAGED4b and FJX1 in various cancer cell lines at protein level.
Figure 10:
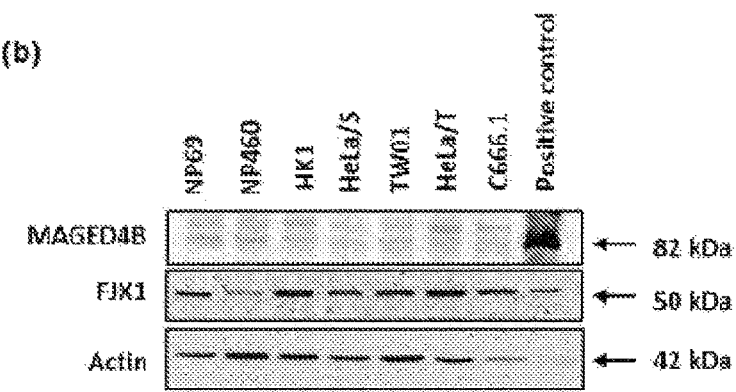
Figure 10:
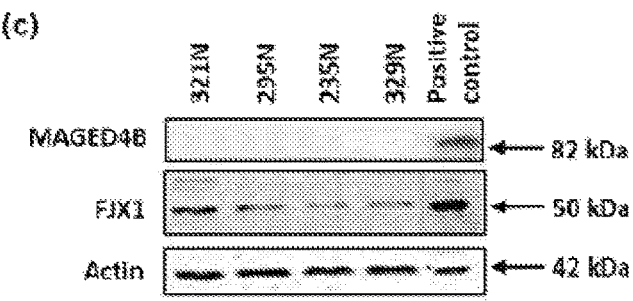
Figure 11:
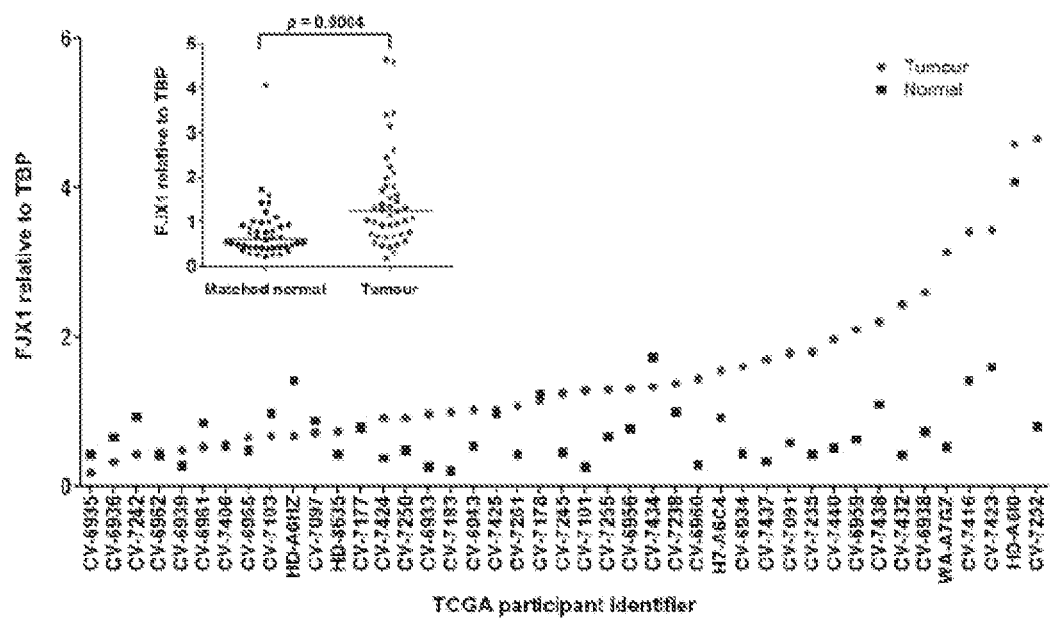
FIG. 11, (a) and (b) show the expression of FJX1 and MAGED4b at transcriptomic level in a set of HNSCC samples with matched normal samples derived from The Cancer Genome Atlas (TCGA) database (https://cancergenome.nih.gov/), normalised against a TATA-Box Binding Protein (TBP).
Figure 11:
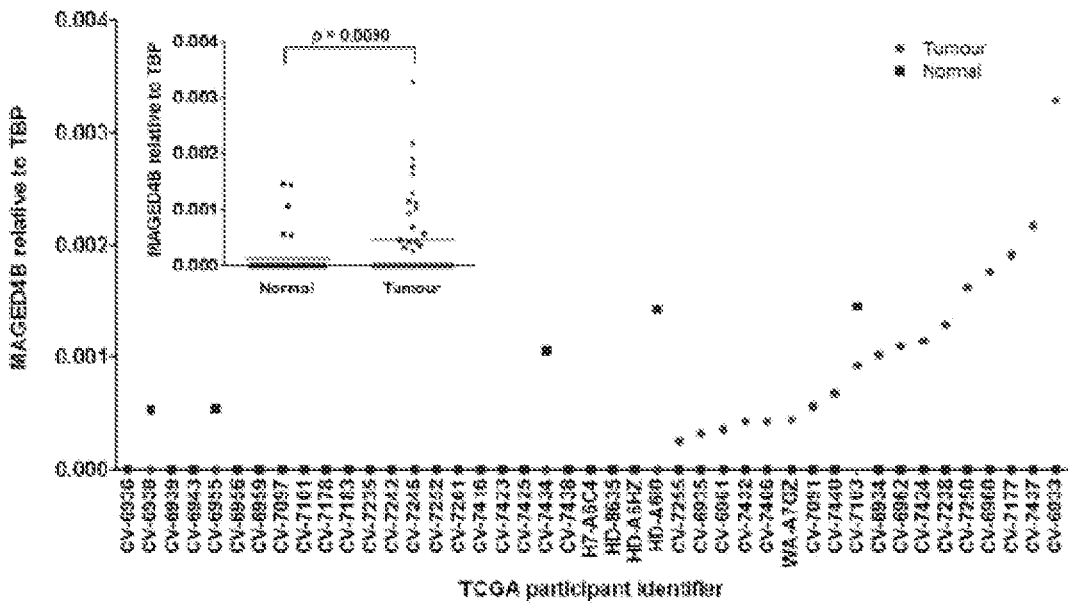

The inventors have previously showed that MAGED4b and FJX1 are overexpressed in OSCC and NPC respectively, whereas the expression is negligible in their respective normal counterparts (Chong et al. 2012; Chong et al. 2009; Ahmad Zabidi M M 2011; Bose et al. 2009). In this study, overexpression was screened in these 2 antigens in an expanded set of HNSCC samples. The data obtained showed that FJX1 is overexpressed in both NPC and OSCC cell lines. As seen in FIG. 9(a), a greater than 2 fold increased at the mRNA level was detected in 5/16 OSCC (ORL-150, ORL-153, ORL-156, ORL-174 and ORL-48) and 6/7 of NPC (HK1, TW01, TW04 and C666.1) and immortalized NP (NP69 and NP460) lines when compared to normal oral keratinocytes and normal nasopharynx tissues respectively. Notably, all OSCC (with exception of ORL-136) and NP/NPC lines were observed to express notable levels of FJX1 at protein level [FIG. 10(a)] compared to normal oral keratinocytes [FIG. 10(c)]. Similarly for MAGED4B, mRNA levels were found to be greater than 2 fold in OSCC cell line ORL-153, the immortalized NP69, and NPC cell line C666.1 [FIG. 9(b)]. Noteworthy, all OSCC (except ORL-195 and ORL-48) and all NPC lines showed marginal expression of MAGED4B at protein level when compared the positive control [cells ectopically overexpressing MAGED4B; FIGS. 10(a) and 10(b)], and in primary cultures of normal oral keratinocytes, no MAGED4B expression was detected [FIG. 10(c)]. The inventors also explored RNAseq data of 43 head and neck cancers with matched normal data from the TOGA database (Cancer Genome Atlas N. 2015) and noted that the more than 60% of the tumour cohort had significant elevated level of FJX1 [FIG. 11(a), p<0.01] and about 40% of the cohort has elevated level of MAGED4B [FIG. 11(b), p<0.01] when compared to the matched normal data.

The inventors next validated these observations for MAGED4B and FJX1 expression levels in commercially obtained TMAs consisting of OSCC and NPC cores (collectively known as HNSCC) and representative staining is shown in FIG. 1(a). Broadly, both MAGED4B and FJX1 expression were detected at protein level, with the staining intensity scores ranging from 0, 1, 2 and 3. The expression of MAGED4B and FJX1 were detected in majority of the OSCC samples (49/49 and 47/49 respectively); while for NPC cases, strong presence of both proteins (MAGED4B; 58/63 and FJX1; 64/74) was detected [Table 7(a)]. When both TMAs were analysed together, the inventors demonstrated as high as 94.7% (89/94) of these HNSCC samples overexpressed either MAGED4B or FJX1 and only 5.3% (5/94) cases were negative for both antigens [Table 7(b)]. However, no significant correlation was found between staining intensity of FJX1 with disease stage or grade of differentiation of the tissues. On the other hand, the levels of expression of MAGED4B is significantly correlated with the grade of differentiation of OSCC samples (p=0.016) and NPC (p=0.007) but not with any disease stage, as seen in the table below.

TABLE 9

Statistical analysis comparing IHC staining intensity with staging and differentiation grade

| Antigens | Parameter tested | NPC | OSCC |
| --- | --- | --- | --- |
| FJX1 | stage (early/late) | p = 0.475 | p = 0.977 |
|  | differentiation grade (I/II/III) | p = 0.051 | p = 0.694 |
| MAGED4B | stage (early/late) | p = 0.913 | p = 0.276 |
|  | differentiation grade (I/II/III) | p = 0.007 | p = 0.016 |

Endogenous T Cells Recognizing PV1 is Presence in HNSCC Patients

Since both MAGED4B and FJX1 were shown to be present in HNSCC patients, it is hypothesised that MAGED4B and/or FJX1 specific CD8+ T cells would also exist. Using the dimer assay, the inventors determined the percentage of CD8+ T cells (CD8+ TCR+ IgG1+) that were able to recognize the PV1 peptides (MAGED4B and FJX1 peptides). The inventors demonstrated the presence of PV1-specific CD8+ T cells in all analyzed HNSCC samples (15/15), the mean ranged from 2.6%-7.1% after normalizing with the non-peptide loaded dimer control (FIG. 2). The average endogenous PV1-specific T cell population detected was higher (7.1%) compared to single F1 (2.6%; p<0.001) or M6-specific T cell (4.6%; p=0.177) population, demonstrating stronger immunogenicity when both peptides were used in combination. No significant differences were observed between the T cell population recognizing the HIV peptide-loaded dimer when compared to non-loaded dimer control (p=0.125). While T cell population recognizing the positive control, FluM peptide-loaded dimer was significantly higher when compared to the non-loaded dimer control (p<0.001).

The inventors then correlate the presence of PV1 specific CD8+ T cells with the expression of MAGED4B and FJX1. The mean percentage of MAGED4B-, FJX1- and MAGED4B & FJX1-antigen specific CD8+ T cells was used as cut off to group patients into high and low antigen specific T cells. The inventors demonstrated about 33% of patients with high levels of antigen-specific T cell recognizing F1, M6 and PV1-loaded dimers, are expressing high levels of both FJX1 and MAGED4B. On the contrary, only 10% of patients with low levels of antigen specific CD8+ T cells expressing highly of both antigens. Strikingly, patients who express minimal of both FJX1 and MAGED4B always showed low percentage of F1, M6 and PV1 antigen specific T cells, as seen in the table below.

TABLE 10

Patients with percentage of CD8+ antigen specific T cells above/below mean percentage in the dimer assay and their antigens (F; FJX1 and M; MAGED4B) expression on tumour tissues. "H" denotes "high expression" and "L" denotes "low/weak expression".

| F1-loaded dimer | | | | M6-loaded dimer | | | | PV1-loaded dimer | | | |
|---|---|---|---|---|---|---|---|---|---|---|---|
| Above mean n = 6 | | Below mean n = 5 | | Above mean n = 3 | | Below mean n = 8 | | Above mean n = 3 | | Below mean n = 8 | |
| F | M | F | M | F | M | F | M | F | M | F | M |
| H | L | H | L | H | L | H | L | H | L | H | H |
| H | H | H | L | H | H | H | H | H | H | H | L |
| H | L | L | L | H | L | H | L | L | H | H | L |
| H | H | H | L | | | H | L | | | H | L |
| L | H | H | L | | | L | L | | | H | L |
| H | L | | | | | H | L | | | L | L |
| | | | | | | H | L | | | H | L |
| | | | | | | L | H | | | H | L |

PV1 Peptides Induces Cytotoxic Cytokines Secretion from HNSCC Patients T Cells In Vitro Next the inventors sought to determine whether the use of PV1 peptide will be able to increase the levels of cytotoxic T cells. In order to determine the efficacy of PV1 in inducing cytotoxic activity in HNSCC patients (n=16; 15 samples overlapped with samples used in HLA-A2: Ig dimer assay), the inventors stimulated patients' T cells in vitro with either M6, F1 or PV1 (F1+M6), and exposed the T cells to target cells expressing MAGED4B (195M) or FJX1 (C666.1F). Prior to any stimulation, ex vivo ELISPOT assay revealed that although peptide-specific T cells were detected in the HLA-A2: Ig dimer assay, the population of IFNγ and Granzyme B cytokine secreting cells (CSCs) prior to stimulation was low [FIG. 3($a$) and 3($b$)]. As seen in FIGS. 3($a$) and 3($b$), after the in vitro stimulation with either M6, F1 or PV1, cytotoxic ELISPOT (CTX ELISPOT) assay showed that the cytolytic activity was increased, resulting in a higher number of cytokine secreting cells for both IFNγ and Granzyme B when compared to the cytokine secreting cells population in the ex vivo ELISPOT. Overall, HNSCC patient T cells response to either M6, F1 or PV1 peptide demonstrate a 2.4 to 39.7 fold increment of cytokine secretion in the cytotoxic ELISPOT assay when compared to prior peptide stimulation. However, the HIV peptide also induces increased levels of IFNγ and Granzyme B secretion after stimulation.

Level of T Cell Activation is Higher in HNSCC Patients Whose Tumours Expressing High MAGED4B and FJX1

Among the 16 patient samples used in the ELISPOT assay, the inventors were able to obtain archived FFPE tumour blocks from 12/16 patients. IHC was then performed to determine the expression of MAGED4B and FJX1 in these tumours. The inventors then divided the patients into 4 groups (FJX1-low, FJX1-high, MAGED4B-low and MAGED4B-high) based on the IHC staining intensity [FIG. 4($a$)], and compared the patients' T cell response in the cytotoxic ELISPOT assay after stimulation with peptides. Staining intensity 0 is categorized as negative, intensity 1 as low expression and intensity 2-3 is considered high expression. Patients with higher expression of FJX1 or MAGED4B demonstrated a higher number of cytokine secreting cells (either IFNγ or Granzyme B) when compared to patients with low expression of FJX1 or MAGED4B [FIG. 4($b$)]. The inventors also found that patient with low levels of both FJX1 and MAGED4B expressions on tissue is less responsive to PV1 stimulation compared to those who express high levels of either FJX1 or MAGED4B on tumour [FIG. 4($c$)]. The data suggests that the immune system of HNSCC patients expressing high levels of either FJX1 or MAGED4B are more readily to be stimulated with PV1 peptide vaccine.

PV1 Might have Beneficiary Effect in Other Cancer Patients

Figure 12:
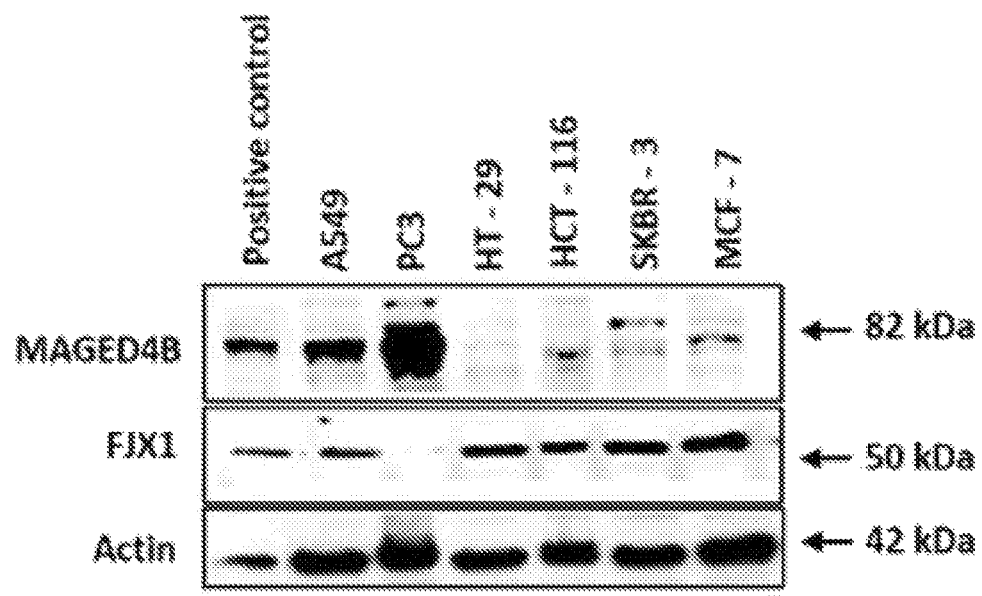
FIG. 12 shows the expression of MAGED4B and FJX1 at protein level in multiple cancer cell lines including lung (A549), prostate (PC3), colorectal (HT-29, HCT-116) and breast (SKBR-3, MCF-7) cancer cell lines.

In order to investigate FJX1 and MAGED4B expression in other cancers and identify potential patient cohorts that might benefit from PV1 therapy, the inventors investigated the expression of MAGED4B and FJX1 using a set of TMA with 5 most common cancers (breast, lung, colon, prostate and rectum cancer). The results demonstrated the expression of MAGED4B was detected in more than 80% of patients in all five cancers and similar observation was seen in FJX1 expression except only ~50% of colon cancer patients were positive for FJX1. When both expressions of both MAGED4B and FJX1 was analyzed collectively, the inventors showed that more than 90% of breast, colon, lung, prostate and rectal tumour tissues had either MAGED4B or FJX1 expression [Table 7($a$)]. Overall, MAGED4B and FJX1 were shown to be overexpressed in breast, colon, lung, prostate and rectal cancer tumours regardless the stage of disease [Table 7($b$)]. Western blotting analysis on these 5 cancer cell lines (A549, lung cancer; PC3, prostate cancer; HT-29, colorectal cancer; HCT-116, colorectal cancer; SKBR-3, breast cancer; MCF-7, breast cancer), showed that MAGED4B expression is high in A549 and PC3 cell lines, while the expression level is weaker in HCT-116, SKBR-3 and MCF-7. On the other hand, FJX1 was shown to express in 5 of 6 cell lines tested (A549, HT-29, HCT-116, SKBR-3 and MCF-7) (FIG. 12) except PC3, suggesting that PV1 might have the potential in targeting these cancers which express MAGED4B and/or FJX1.

Discussion

Many tumours tend to harbour deregulated expression of proteins that normally only expresses in immune-privileged sites such as testis (Inaoka et al. 2011; Gjerstorff et al. 2015) and during embryogenesis (Lawrence et al. 2011; Becker et al. 2012). The unique expression of these antigens, making them a good target for cancer therapy. Our previous studies identified 2 tumour antigens, FJX1 and MAGED4B, which involved in such processes, with negligible expression in normal but overexpressed in NPC and OSCC respectively (Chai et al. 2015; Chong et al. 2012). In this study, the inventors expended the cohort to a larger number of cell lines and tumour samples. The IHC data demonstrated that most of the OSCC and NPC tumours has overexpression of either MAGED4B or FJX1. FJX1 is shown to overexpress in both HNSCC cell lines and tumour tissue. But for MAGED4B, despite IHC staining showed positive staining in a large number of HNSCC tumour tissues, the expression levels of MAGED4B detected was low in HNSCC cancer cell lines. This could be due to the loss of antigen in long term culturing environment. Further correlative studies revealed that MAGED4B expression is correlated with the grade of tumour differentiation but the inventors did not find any significant correlation between the expressions of the 2 antigens with patients' disease staging. As OSCC and NPC made up to most of the head and neck cancer (HNSCC) cases, the inventors hypothesized that both MAGED4B and FJX1 could be important targets for HNSCC. In summary, inventors confirmed that these two antigens is overexpressed in ~90% of HNSCC patients and served as good therapeutic target for HNSCC patients. On top of this, the inventors also showed that MAGED4B and FJX1 are presence in tumour of other cancer types, including breast, colon, lung, prostate and rectum cancers, indicating that targeting these 2 antigens not only could benefit HNSCC patients, but also potentially benefit patients who suffer from breast, colon, lung, prostate and rectum cancers.

The inventors designed a MAGED4B-specific and FJX1-specific peptide vaccine to target OSCC and NPC respectively. The inventors showed that pulsing of PBMC from OSCC and NPC patients with peptide vaccine derived from MAGED4B and FJX1 respectively were able to elicit cytotoxic immune response against target cancer cells. However, due to the heterogeneity nature of tumours and likelihood of cancer cells losing antigen expression as they progress (Cecco et al. 2011), targeting single tumour antigen as treatment modality is always insufficient. In order to overcome such limitations, it is important to target multiple antigens to induce broader immune response, to ensure that most tumour can be eradicated, to avoid selection of antigen negative clones (Gerdemann et al. 2011), and at the same time benefiting a larger patient cohort. Previous studies on esophageal cancer patients showed that multiple antigens peptide vaccine can elicit a more robust immune response in patients. Patients who have CTL responses to multiple antigens peptide vaccine confers to better overall survival compared to those having CTL responses against single antigen peptides (Kono et al. 2012). In the current study, the inventors combined peptides of both MAGED4b and FJX1 (named as PV1) and sought to test PV1 efficacy as a dual-antigen peptide vaccine targeting head and neck cancer patients.

The inventor's results showed that the dual-antigen vaccine PV1 is more immunogenic compared to single peptides. Larger population of inherent T cells are able to recognize PV1 when compared to either M6 or F1 peptide alone in the dimer assay. The inventors also observed that although the ability of T cells to secrete IFNγ and granzyme B was dampened prior to peptide stimulation in vitro, the levels of IFNγ and granzyme B secreting T cells populations increased in the cytotoxic ELISPOT assay. IFNγ and granzyme B secretion after PV1 stimulation was as high as, if not, better compared to stimulation by single peptide. In summary, the use of dual antigen peptides comprises of both MAGED4B and FJX1 peptides against head and neck cancer lines is compelling and warrant further development to benefit patients. The inventors also observed the priming of T cells by irrelevant HIV-gag protein peptide, inducing unspecific IFNγ and granzyme B secretion from T cells. As reported previously by Karlsson et al. 2004, the inventors hypothesized that this unspecific stimulation was due to the poorly soluble peptide that induces false positive response upon stimulation in vitro. Hence, poorly soluble HIV peptide might not be a good irrelevant peptide control for cytotoxic ELISPOT assay after peptide stimulation.

Importantly, the inventor's data showed that T cells from patients with higher levels of antigen expression are more readily to be re-sensitized, and having better response upon PV1 stimulation. This encouraging data indicates PV1 functions in antigen specific manner, and patient screening based on the expression level or the presence of either MAGED4B or FJX1 on the tumour would be an important inclusion criteria for the PV1 therapy.

Recently, two immune checkpoint inhibitors were granted approval by U.S. Food and Drug Administration as treatment for the HNSCC. Nivolumab (OPDIVO, Bristol-Myers Squibb Company) was approved in November 2016 and Pembrolizumab (KEYTRUDA, Merck & Co., Inc.) was granted accelerated approval earlier in August 2016. However, response rate of HNSCC patients receiving these drugs were reported only as low as 13% (OPDIVO, Bristol-Myers Squibb Company) (Ferris et al. 2016) and 16% (KEYTRUDA, Merck & Co., Inc.) (U.S. Food and Drug Administration 2016). Due to the complexity of immune system that always maintain a check and balance between immune activation and suppression (Chen L and Flies D B, 2013), using immune checkpoint inhibitors alone to release the brake of immune response might not be sufficient to reactivate the already dampened immune system in patients. Combination with an immunogenic immune activator such as cancer vaccines derived from tumour antigens has been reported to be more efficiently activate the immune response by altering the effector T cells to regulatory T cells ratio, increasing antigen-specific T cells (Morse and Lyerly, 2015; Mkrtichyan et al. 2011; Avogadri et al. 2014; Karyampudi et al. 2014). As demonstrated by the inventors, the dual-antigen PV1 peptide vaccine is immunogenic and is capable of inducing anti-tumour immune responses among HNSCC patients, suggesting that combination of immune checkpoint inhibitors with PV1 might enhance the response rate in HNSCC patients.

However, different peptides could have different binding affinity towards the MHC molecules, and hence might cause competition in binding to the epitopes. Therefore a better formulation to ensure both epitopes of FJX1 and MAGED4B peptides are presented, or a better strategy in administrating the vaccine, such as to administer at different site of the body should be considered and warrant further investigation. Overall, the inventors' results showed that PV1 performed at comparable level, or even better compared to single peptide. HNSCC patients with tumours expressing either FJX1 or MAGED4B could benefit from the vaccine. Our data also suggests that PV1 might also benefit patients of other cancer types including breast, lung, prostate, colon and rectum cancers. The optimal dosage to induce sufficient immune response and the efficacy of PV1 to control tumour burden is currently under evaluation using transgenic in vivo model.

Example 2

Evaluation of PV1 in Animal Model
PV1 does not Increase Unwanted Inflammatory Response Prior to the evaluation of PV1 immunogenicity using animal model, Griess assay that measure inflammatory responses was used to assess the toxicity of M6 and F1 peptides. Mouse macrophage cell line RAW264.7 was treated with various concentration of M6, F1 or PV1 peptides: 25 µg/ml, 50 µg/ml and 100 µg/ml and 10% DMSO in PBS was used as negative control while 1 ng/ml of lipopolysaccharides (LPS) was used as a positive control. The degree of inflammation was indirectly measured based on the levels of inducible nitric oxide synthase (iNOS) produced by RAW264.7 cells.

FIG. 5(a) shows the degree of inflammation induced by M6 or F1 peptides on RAW 264.7. The production of nitrite by RAW264.7 in the presence of M6 was at least 7 fold lower than those received LPS stimulation (P<0.01). The same trend observed in the F1 treatment group as well in which the amount of nitrite released was 10 fold lower than positive control (P<0.05). This suggested that the M6 and F1 do not stimulate the upregulation of iNOS expression which further indicated that the degree of inflammation induced by these two target peptide was low. When M6 and F1 combined as PV1, our result consistently showed that the amount of iNOS accumulation in the PV1 treatment group was significant lower than those in LPS treatment group (10 fold differences, P<0.05) [FIG. 5(b)]. Griess assay results showed that PV1 did not induce inflammation in vitro settings.

PV1 Vaccination Increase Activation of Antigen-Specific T Cells

The dual-antigens PV1 comprised of MAGED4B peptide 6 (M6) and FJX1 peptide 1 (F1) was shown to be immunogenic when tested using peripheral blood mononuclear cell (PBMC) extracted from HNSCC patients. This study was aim to evaluate the immunogenicity and efficacy of PV1 using transgenic mouse model B6.Cg-Tg(HLA-A/H2-D) 2Enge/J, which which enables the modeling of human T-cell immune responses to HLA-A2 presented antigens.

Mice were vaccinated weekly for 3 consecutive weeks (3 doses) with 5 different treatment groups as shown in Table 6 above. At week 4, mice were sacrificed and the immune cells was harvested from mice spleen. The presence of IFNγ-secreting peptide specific CD8+ T cells of vaccinated mice was determined using dimer assay and compare with the vehicle control group.

The results showed that PV1 is immunogenic. Animals vaccinated with as low as 500 µg PV1 showed high recognition towards PV1-loaded dimers compared to vehicle control animals (5% DMSO in phosphate buffered saline, PBS). This response is peptide specific as the vaccinated mice showed a baseline/negligible response when expose to non-loaded and irrelevant peptide (HIV) loaded dimer, as illustrated in FIG. 6(a).

Using ELISPOT assay, the inventors evaluated the population of T-cells that is capable of carry out cytotoxic function to kill cancer cells presenting the peptides post-vaccination. Vaccinated animals are able to recognize T2 cells-presenting the PV1 and execute killing activity against these T2 cells at dose dependent manners [FIG. 6(b)], suggesting that the PV1 vaccination has successfully increased the recognition of T cells in these animals PV1 is Safe and No Adverse Events Observed in Vaccinated Mice Animal weight was taken twice a week during the period of vaccination. The inventors did not observe any weight-loss or adverse events during the 4-week period of immunization in all treatment groups [FIG. 7(a)].

Pathological report of major organs (heart, lungs, kidney, liver and spleen) harvested from all treatment group mice showed all PV1-treated mice were within normal limit. No local toxicity observed in these animals [FIG. 7(b)].

PV1 Delayed Tumour Growth in Mice

In previous immunogenicity study, the inventors showed that PV1 is able to induce antigen-specific T-cell response at concentration as low as 500 µg. Therefore, 1000 µg PV1 was used in the subsequent assay to determine the efficacy of PV1 in reducing tumour burden in mice.

A total of $1 \times 10^6$ cells of syngeneic B16 melanoma cell expressing AAD and MAGED4B genes was transplanted onto the mice. After the tumour size reached 30-50 mm$^3$, mice were randomly assigned to 2 groups. Treatment group mice received 1000 µg PV1 with IFA while the vehicle control groups received 5% DMSO in PBS.

Tumour size was measured twice weekly and mice treated with 1000 µg PV1+IFA showed delayed tumour growth when compared to the vehicle control (VC) group (FIG. 8).

REFERENCES

Ferlay J, Soerjomataram I, Dikshit R, Eser S, Mathers C, Rebelo M, et al. Cancer incidence and mortality worldwide: sources, methods and major patterns in GLOBOCAN 2012. *International journal of cancer* 2015; 136(5): E359-86 doi 10.1002/ijc.29210.

Vermorken J B, Mesia R, Rivera F, Remenar E, Kawecki A, Rottey S, et al. Platinum-based chemotherapy plus cetuximab in head and neck cancer. *The New England journal of medicine* 2008; 359(11):1116-27 doi 10.1056/NEJMoa0802656.

Nasman A, Romanitan M, Nordfors C, Grun N, Johansson H, Hammarstedt L, et al. Tumor infiltrating CD8+ and Foxp3+ lymphocytes correlate to clinical outcome and human papillomavirus (HPV) status in tonsillar cancer. *PLoS One* 2012; 7(6):e38711 doi 10.1371/journal.pone.0038711.

Ferris R L, Blumenschein G, Jr., Fayette J, Guigay J, Colevas A D, Licitra L, et al. Nivolumab for Recurrent Squamous-Cell Carcinoma of the Head and Neck. *The New England journal of medicine* 2016 doi 10.1056/NEJMoa1602252.

Slingluff C L, Jr. The present and future of peptide vaccines for cancer: single or multiple, long or short, alone or in combination? *Cancer journal* 2011; 17(5):343-50 doi 10.1097/PPO.0b013e318233e5b2.

Yoshitake Y, Fukuma D, Yuno A, Hirayama M, Nakayama H, Tanaka T, et al. Phase II clinical trial of multiple peptide vaccination for advanced head and neck cancer patients revealed induction of immune responses and improved OS. *Clinical cancer research:* 2015; 21(2):312-21 doi 10.1158/1078-0432.CCR-14-0202.

Ye F, Chen C, Qin J, Liu J, Zheng C. Genetic profiling reveals an alarming rate of cross-contamination among human cell lines used in China. *The FASEB journal:* 2015; 29(10):4268-72 doi 10.1096/fj.14-266718.

Charafe-Jauffret E, Tarpin C, Bardou V J, Bertucci F, Ginestier C, Braud A C, et al. Immunophenotypic analysis of inflammatory breast cancers: identification of an 'inflammatory signature'. *The Journal of pathology* 2004; 202(3):265-73 doi 10.1002/path.1515.

Lim K P, Chun N A, Gan C P, Teo S H, Rahman Z A, Abraham M T, et al. Identification of immunogenic MAGED4B peptides for vaccine development in oral cancer immunotherapy. *Human vaccines & immunotherapeutics* 2014; 10(11): 3214-23 doi 10.4161/hv.29226.

Chong C E, Lim K P, Gan C P, Marsh C A, Zain R B, Abraham M T, et al. Over-expression of MAGED4B increases cell migration and growth in oral squamous cell carcinoma and is associated with poor disease outcome. *Cancer letters* 2012; 321(1):18-26 doi 10.1016/j.canlet.2012.03.025.

Cheong S C, Chandramouli G V, Saleh A, Zain R B, Lau S H, Sivakumaren S, et al. Gene expression in human oral squamous cell carcinoma is influenced by risk factor exposure. *Oral oncology* 2009; 45(8):712-9 doi 10.1016/j.oraloncology.2008.11.002.

Ahmad Zabidi M M. Identification of four-jointed box 1 as a potential oncogene in nasopharyngeal carcinoma. M.Sc. Thesis. Kuala Lumpur. (http://pendeta.um.edu.my/client/default/search/detailnonmodal/ent:$002f$002fSD_ILS$-002f871$002fSD_ILS:871872/onejsessionid=55866C8-DEF2376DCA6A645D4DCFFDBE1.enterprise-202-00?qu=%22871872%22&te=ILS): University of Malaya; 2011. 100 p.

Bose S, Yap L F, Fung M, Starzcynski J, Saleh A, Morgan S, et al. The ATM tumour suppressor gene is down-regulated in EBV-associated nasopharyngeal carcinoma. *The Journal of pathology* 2009; 217(3):345-52 doi 10.1002/path.2487.

Cancer Genome Atlas N. Comprehensive genomic characterization of head and neck squamous cell carcinomas. *Nature* 2015; 517(7536):576-82 doi 10.1038/nature14129.

Inaoka R J, Jungbluth A A, Baiocchi O C, Assis M C, Hanson N C, Frosina D, et al. An overview of cancer/testis antigens expression in classical Hodgkin's lymphoma (cHL) identifies MAGE-A family and MAGE-C1 as the most frequently expressed antigens in a set of Brazilian cHL patients. *BMC cancer* 2011; 11(1):416 doi 10.1186/1471-2407-11-416.

Gjerstorff M F, Andersen M H, Ditzel H J. Oncogenic cancer/testis antigens: prime candidates for immunotherapy. *Oncotarget* 2015; 6(18):15772-87 doi 10.18632/oncotarget.4694.

Lawrence M G, Margaryan N V, Loessner D, Collins A, Kerr K M, Turner M, et al. Reactivation of embryonic nodal signaling is associated with tumor progression and promotes the growth of prostate cancer cells. *The Prostate* 2011; 71(11):1198-209 doi 10.1002/pros.21335.

Becker D, Sfakianakis I, Krupp M, Staib F, Gerhold-Ay A, Victor A, et al. Genetic signatures shared in embryonic liver development and liver cancer define prognostically relevant subgroups in HCC. *Molecular cancer* 2012; 11:55 doi 10.1186/1476-4598-11-55.

Chai S J, Yap Y Y, Foo Y C, Yap L F, Ponniah S, Teo S H, et al. Identification of Four-Jointed Box 1 (FJX1)-Specific Peptides for Immunotherapy of Nasopharyngeal Carcinoma. *PloS one* 2015; 10(11):e0130464 doi 10.1371/journal.pone.0130464.

Cecco S, Muraro E, Giacomin E, Martorelli D, Lazzarini R, Baldo P, et al. Cancer vaccines in phase II/III clinical trials: state of the art and future perspectives. *Current cancer drug targets* 2011; 11(1):85-102.

Gerdemann U, Katari U, Christin A S, Cruz C R, Tripic T, Rousseau A, et al. Cytotoxic T lymphocytes simultaneously targeting multiple tumor-associated antigens to treat EBV negative lymphoma. *Molecular therapy* 2011; 19(12):2258-68 doi 10.1038/mt.2011.167.

Kono K, Iinuma H, Akutsu Y, Tanaka H, Hayashi N, Uchikado Y, et al. Multicenter, phase II clinical trial of cancer vaccination for advanced esophageal cancer with three peptides derived from novel cancer-testis antigens. *Journal of translational medicine* 2012; 10:141 doi 10.1186/1479-5876-10-141.

FDA US. Pembrolizumab (KEYTRUDA). U.S. Food and Drug Administration: http://www.fda.gov/Drugs/InformationOnDrugs/ApprovedDrugs/ucm515627.htm; 2016. p http://www.fda.gov/Drugs/InformationOnDrugs/ApprovedDrugs/ucm515627.htm.

Chen L, Flies D B. Molecular mechanisms of T cell co-stimulation and co-inhibition. *Nature reviews Immunology* 2013; 13(4):227-42 doi 10.1038/nri3405.

Morse M A, Lyerly H K. Checkpoint blockade in combination with cancer vaccines. *Vaccine* 2015; 33(51):7377-85 doi 10.1016/j.vaccine.2015.10.057.

Mkrtichyan M, Najjar Y G, Raulfs E C, Abdalla M Y, Samara R, Rotem-Yehudar R, et al. Anti-PD-1 synergizes with cyclophosphamide to induce potent anti-tumor vaccine effects through novel mechanisms. *European journal of immunology* 2011; 41(10):2977-86 doi 10.1002/eji.201141639.

Avogadri F, Zappasodi R, Yang A, Budhu S, Malandro N, Hirschhorn-Cymerman D, et al. Combination of alphavirus replicon particle-based vaccination with immunomodulatory antibodies: therapeutic activity in the B16 melanoma mouse model and immune correlates. *Cancer immunology research* 2014; 2(5):448-58 doi 10.1158/2326-6066.CIR-13-0220.

Karyampudi L, Lamichhane P, Scheid A D, Kalli K R, Shreeder B, Krempski J W, et al. Accumulation of memory precursor CD8 T cells in regressing tumors following combination therapy with vaccine and anti-PD-1 antibody. *Cancer research* 2014; 74(11):2974-85 doi 10.1158/0008-5472.CAN-13-2564.

The invention claimed is:

1. A peptide composition,
comprising at least a Four-jointed Box 1 (FJX1) peptide and a Melanoma antigen family D4b (MAGED4b) peptide,
wherein the peptide composition binds with major histocompatibility complex (MHC) Class I molecules for inducing an anti-cancer immune response in a subject,
wherein the FJX1 peptide comprises a peptide sequence of SEQ ID NO.1, and the MAGED4b peptide comprises a peptide sequence of SEQ ID NO. 2.

2. The peptide composition according to claim 1, wherein the MHC class I molecules are human leukocyte antigen A2 (HLA-A2) molecules.

3. The peptide composition according to claim 1, wherein the peptide composition binds with the MHC Class I molecules to increase cytokine secreting cells in the subject for inducing the anti-cancer response in the subject.

4. The peptide composition according to claim 3, wherein the cytokine comprises of interferon gamma (IFNγ) and granzyme B.

5. The peptide composition according to claim 1, wherein the anti-cancer immune response is induced in the subject when FJX1 and/or MAGED4b are expressed by a cancer cell.

6. The peptide composition according to claim 5, wherein the cancer cells are head and neck squamous cell carcinoma (HNSCC) cells, breast cancer cells, colon cancer cells, rectum cancer cells, lung cancer cells, prostate cancer cells, or any combination thereof.

7. A vaccine comprising at least a FJX1 peptide and a MAGED4b peptide as set forth in claim 1.

8. The vaccine according to claim 7, wherein the vaccine may be used in combination with cancer therapeutic treatments.

9. The vaccine according to claim 8 comprising immune checkpoint inhibitors.

10. The vaccine according to claim 9, wherein the immune checkpoint inhibitors comprise anti-PD-1 antibodies.

11. The vaccine according to claim 8, wherein the anti-cancer immune response is induced when cancer cells of head and neck squamous cell carcinoma (HNSCC), breast cancer, colon cancer, rectum cancer, lung cancer, prostate cancer, or any combination therefore is detected in the subject.

12. A method of manufacturing a medicament for treating head and neck squamous cell carcinoma (HNSCC), breast cancer, colon cancer, rectum cancer, lung cancer, prostate cancer, or any combination thereof in a subject in need thereof, comprising:
making the medicament using an effective amount of a Four-jointed Box 1 (FJX1) peptide and a Melanoma antigen family D4b (MAGED4b) peptide, wherein the medicament is capable of binding with major histocompatibility complex (MHC) class I molecules to induce an anti-cancer immune response in the subject;
wherein the FJX1 peptide comprises a peptide sequence of SEQ ID NO.1, and the MAGED4b peptide comprises a peptide sequence of SEQ ID NO. 2.

* * * * *

SEQUENCE LISTING

<160> NUMBER OF SEQ ID NOS: 4

<210> SEQ ID NO 1
<211> LENGTH: 11
<212> TYPE: PRT
<213> ORGANISM: Unknown
<220> FEATURE:
<223> OTHER INFORMATION: A peptide sequence of the FJX1 gene specific to human leukocyte antigen A2 epitope https://www.ncbi.nlm.nih.gov/

```
    protein/NP_055159.2 (located at aa15-aa25)

<400> SEQUENCE: 1

Trp Leu Leu Ala Leu Gly Ser Leu Leu Ala Leu
1               5                   10

<210> SEQ ID NO 2
<211> LENGTH: 9
<212> TYPE: PRT
<213> ORGANISM: Unknown
<220> FEATURE:
<223> OTHER INFORMATION: A peptide sequence of the MAGED4B gene specific
      to human leukocyte antigen A2 epitope https://www.ncbi.nlm.nih.
      gov/protein/NP_803879.1 (located at aa501-aa509)

<400> SEQUENCE: 2

Arg Leu Ser Leu Leu Leu Val Ile Leu
1               5

<210> SEQ ID NO 3
<211> LENGTH: 9
<212> TYPE: PRT
<213> ORGANISM: Influenza A virus

<400> SEQUENCE: 3

Gly Ile Leu Gly Phe Val Phe Thr Leu
1               5

<210> SEQ ID NO 4
<211> LENGTH: 9
<212> TYPE: PRT
<213> ORGANISM: Human immunodeficiency virus

<400> SEQUENCE: 4

Ser Leu Tyr Asn Thr Tyr Ala Thr Leu
1               5
```